(12) United States Patent | (10) Patent No.: US 12,588,965 B2
Ichii et al. | (45) Date of Patent: Mar. 31, 2026

(54) ROBOTIC SURGICAL SYSTEM AND CONTROL METHOD OF ROBOTIC SURGICAL SYSTEM

(71) Applicant: KAWASAKI JUKOGYO KABUSHIKI KAISHA, Kobe (JP)

(72) Inventors: Tetsuo Ichii, Kobe (JP); Takahiro Ueno, Kobe (JP); Takuya Shitaka, Kobe (JP); Akinori Igarashi, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 491 days.

(21) Appl. No.: 17/898,511

(22) Filed: Aug. 30, 2022

(65) Prior Publication Data

US 2022/0409317 A1     Dec. 29, 2022

(30) Foreign Application Priority Data

Aug. 31, 2021     (JP) ................................. 2021-141034

(51) Int. Cl.
*A61B 34/00* (2016.01)
*A61B 34/30* (2016.01)
*A61B 34/35* (2016.01)
*B25J 9/16* (2006.01)

(52) U.S. Cl.
CPC .............. *A61B 34/77* (2016.02); *A61B 34/35* (2016.02); *B25J 9/1651* (2013.01); *B25J 9/1689* (2013.01); *A61B 2034/305* (2016.02)

(58) Field of Classification Search
None
See application file for complete search history.

(56) References Cited

U.S. PATENT DOCUMENTS

| | | | |
|---|---|---|---|
| 6,977,630 B1 * | 12/2005 | Donath ................ | G01C 21/365 |
| | | | 345/9 |
| 6,994,703 B2 * | 2/2006 | Wang ..................... | A61B 34/71 |
| | | | 606/7 |
| 11,076,923 B1 * | 8/2021 | Adelman ............... | B25J 9/1689 |
| 2003/0004610 A1 | 1/2003 | Niemeyer et al. | |
| 2014/0277741 A1 | 9/2014 | Kwon et al. | |
| 2019/0160668 A1 * | 5/2019 | Oyama .................. | B25J 13/084 |
| 2019/0269476 A1 * | 9/2019 | Bowling ............... | A61B 34/20 |

(Continued)

FOREIGN PATENT DOCUMENTS

| | | |
|---|---|---|
| JP | 2014-180751 A | 9/2014 |
| JP | 2020-532385 A | 11/2020 |

(Continued)

OTHER PUBLICATIONS

Hardesty, L. (2013) Explained: Matrices, MIT News | Massachusetts Institute of Technology. Available at: https://news.mit.edu/2013/explained-matrices-1206 (Accessed: Apr. 24, 2025). (Year: 2013).*

*Primary Examiner* — Erica S Lee
(74) *Attorney, Agent, or Firm* — METROLEX IP LAW GROUP, PLLC; Robert L. Scott, Esq.

(57) ABSTRACT

In a robotic surgical system, a control device is configured or programmed to perform first scaling on at least a rotational component in a received operation amount, and calculate a rotation angle of a joint axis of a robot arm by performing an inverse kinematics calculation on a translational component and the rotational component after the first scaling is performed.

17 Claims, 18 Drawing Sheets

(56)                    References Cited

U.S. PATENT DOCUMENTS

| | | | |
|---|---|---|---|
| 2020/0078133 A1* | 3/2020 | Flossmann | ............... G06T 7/70 |
| 2020/0179068 A1 | 6/2020 | Peine et al. | |
| 2021/0137624 A1* | 5/2021 | Maret | ................... A61B 34/74 |
| 2021/0297560 A1* | 9/2021 | Luna | ..................... A61B 34/77 |
| 2021/0378769 A1* | 12/2021 | Zhou | ..................... B25J 9/1689 |
| 2023/0310108 A1* | 10/2023 | Balter | ................... A61B 34/74 |
| | | | 606/1 |

FOREIGN PATENT DOCUMENTS

| | | |
|---|---|---|
| JP | 2021-502264 A | 1/2021 |
| WO | 2019/117855 A1 | 6/2019 |

* cited by examiner

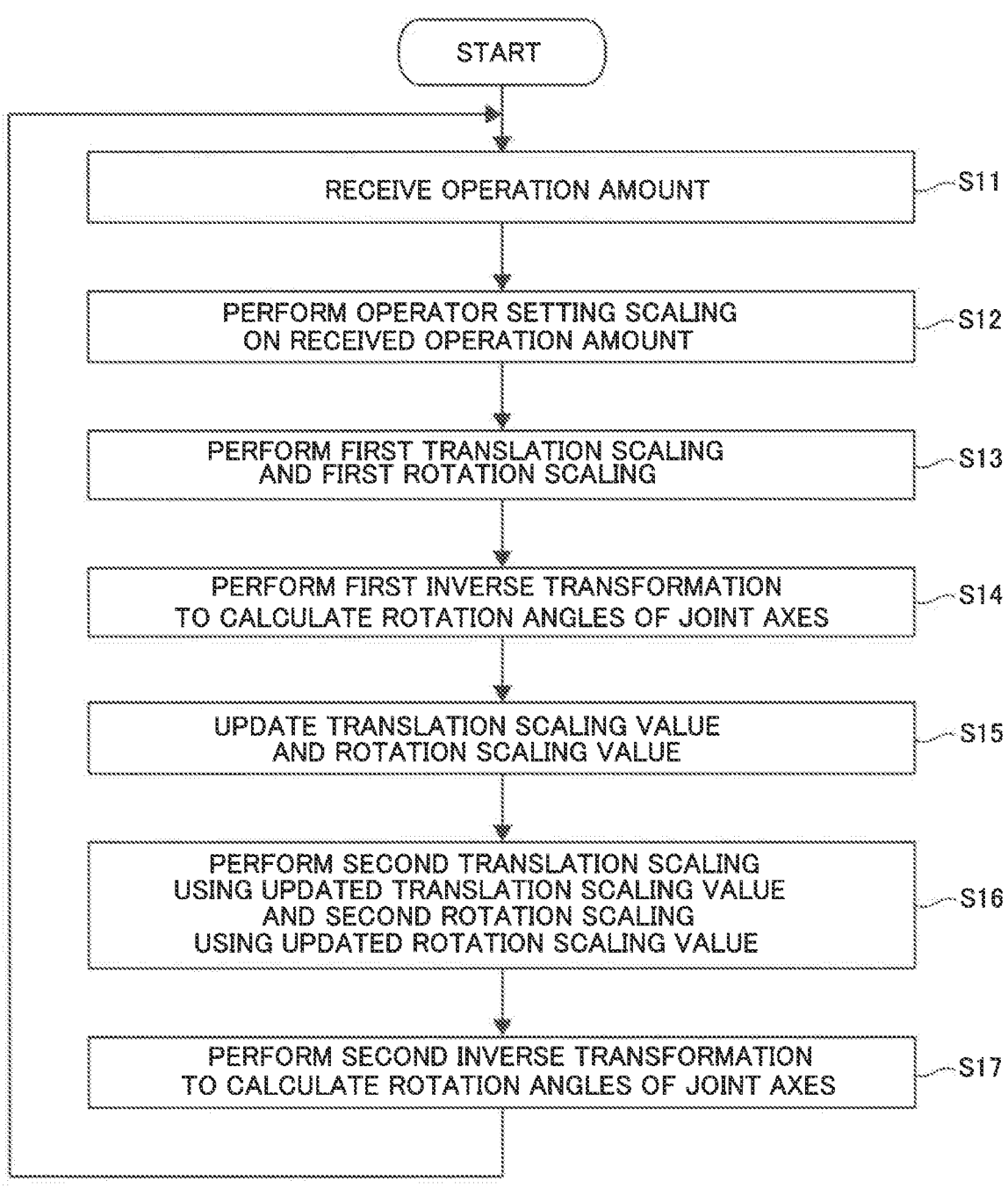

START

RECEIVE OPERATION AMOUNT — S11

PERFORM OPERATOR SETTING SCALING
ON RECEIVED OPERATION AMOUNT — S12

PERFORM FIRST TRANSLATION SCALING
AND FIRST ROTATION SCALING — S13

PERFORM FIRST INVERSE TRANSFORMATION
TO CALCULATE ROTATION ANGLES OF JOINT AXES — S14

UPDATE TRANSLATION SCALING VALUE
AND ROTATION SCALING VALUE — S15

PERFORM SECOND TRANSLATION SCALING
USING UPDATED TRANSLATION SCALING VALUE
AND SECOND ROTATION SCALING
USING UPDATED ROTATION SCALING VALUE — S16

PERFORM SECOND INVERSE TRANSFORMATION
TO CALCULATE ROTATION ANGLES OF JOINT AXES — S17

*FIG.26*

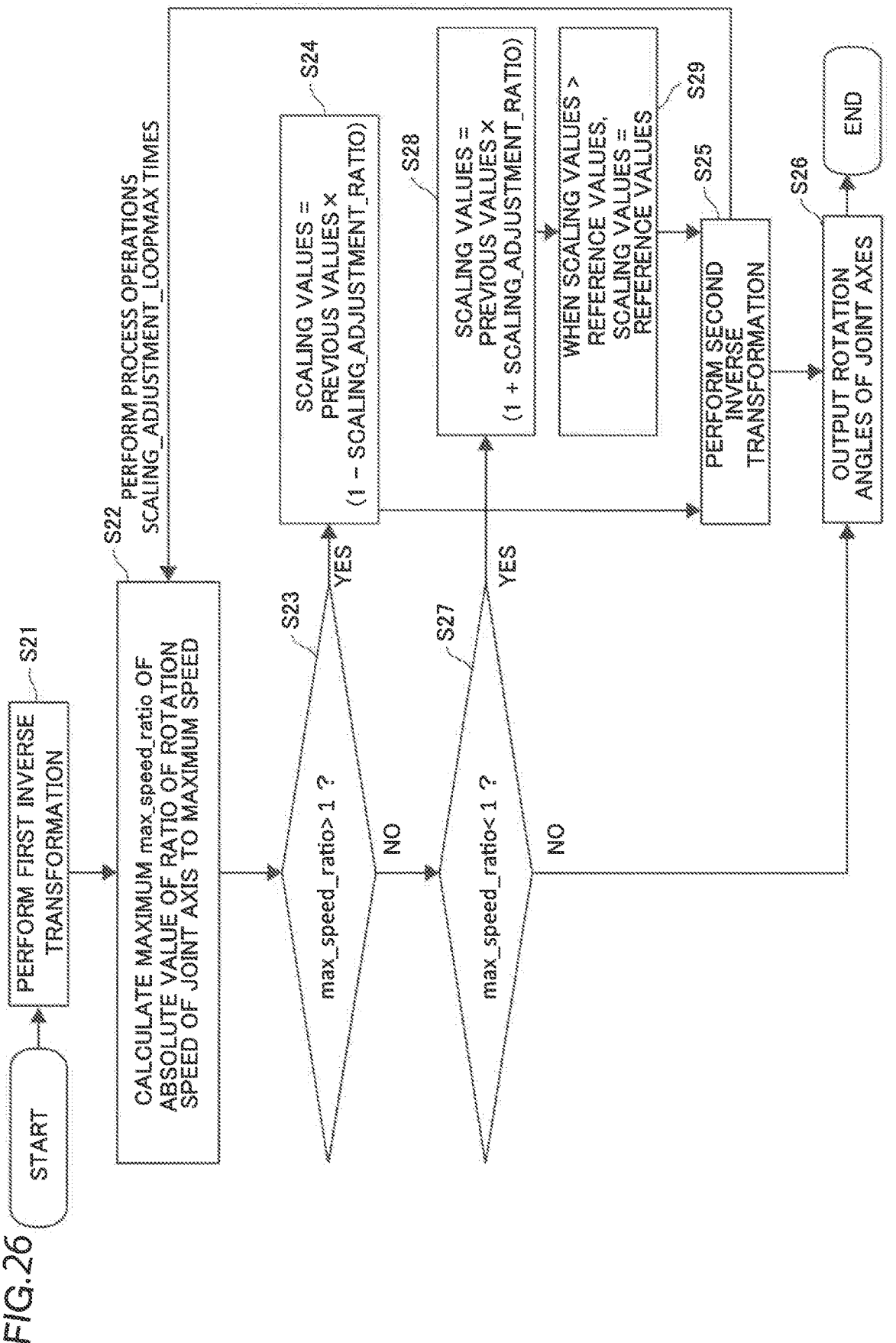

START

S21 PERFORM FIRST INVERSE TRANSFORMATION

S22 CALCULATE MAXIMUM max_speed_ratio OF ABSOLUTE VALUE OF RATIO OF ROTATION SPEED OF JOINT AXIS TO MAXIMUM SPEED

PERFORM PROCESS OPERATIONS SCALING_ADJUSTMENT_LOOPMAX TIMES

S23 max_speed_ratio> 1 ?

YES

NO

S24 SCALING VALUES = PREVIOUS VALUES × (1 − SCALING_ADJUSTMENT_RATIO)

S27 max_speed_ratio< 1 ?

YES

NO

S28 SCALING VALUES = PREVIOUS VALUES × (1 + SCALING_ADJUSTMENT_RATIO)

S29 WHEN SCALING VALUES > REFERENCE VALUES, SCALING VALUES = REFERENCE VALUES

S25 PERFORM SECOND INVERSE TRANSFORMATION

S26 OUTPUT ROTATION ANGLES OF JOINT AXES

END

ROBOTIC SURGICAL SYSTEM AND CONTROL METHOD OF ROBOTIC SURGICAL SYSTEM

CROSS-REFERENCE TO RELATED APPLICATION

The present application claims priority to JP2021-141034, which is incorporated herein by reference.

BACKGROUND OF THE INVENTION

Field of the Invention

The present disclosure relates to a robotic surgical system and a control method of a robotic surgical system, and more particularly, it relates to a robotic surgical system including an operation unit to receive an operation of an operator, and a control method of the robotic surgical system.

Description of the Background Art

Conventionally, a robotic surgical system including a master handle to receive an operation of an operator is known. In U.S. Pat. No. 6,994,703, a surgeon moves a master handle to move an end effector attached to a robot arm. In U.S. Pat. No. 6,994,703, scaling is performed such that the movement amount of the end effector is smaller than the movement amount of the master handle moved by the surgeon. Specifically, when the surgeon moves the master handle, a control device calculates a difference value between the position of the master handle after the movement and the position of the master handle before the movement. Then, the control device multiplies the calculated difference value by a scale factor. The scale factor is less than 1. The control device moves the end effector based on the difference value multiplied by the scale factor. The scale factor is less than 1, and thus the movement amount of the end effector is smaller than the movement amount of the master handle moved by the surgeon.

In a conventional robotic surgical system as described in U.S. Pat. No. 6,994,703, when a surgeon moves a master handle, a control device performs an inverse kinematics calculation on a translational component for translation of an end effector and a rotational component for rotation of the end effector in an operation amount received by the master handle to calculate the rotation angles of joint axes of a robot arm. In U.S. Pat. No. 6,994,703, scaling is performed by multiplying a difference value between the position of the master handle after the movement and the position of the master handle before the movement by a scale factor. Here, a change in position is a translational movement, and thus scaling is performed only on the translational component of the end effector. Depending on the posture of the robot arm, the posture of the robot arm may change significantly even when movement of the tip end of the end effector is relatively small. In such a case, when scaling is performed only on translation as in U.S. Pat. No. 6,994,703, scaling may not be effectively performed for the posture of the robot arm.

SUMMARY OF THE INVENTION

The present disclosure is intended to solve the above problem. The present disclosure aims to provide a robotic surgical system and a control method of a robotic surgical system each capable of effectively scaling the posture of a robot arm.

In order to attain the aforementioned object, a robotic surgical system according to a first aspect of the present disclosure includes a patient-side apparatus including a robot arm having a tip end to which a surgical instrument is attached, an operator-side apparatus including an operation unit to receive an operation amount for the surgical instrument, and a control device configured or programmed to control translation and rotation of the surgical instrument based on the received operation amount. The control device is configured or programmed to perform first scaling on at least a rotational component of a translational component and the rotational component of the surgical instrument in the received operation amount, and calculate a rotation angle of a joint axis of the robot arm by performing an inverse kinematics calculation on the translational component and the rotational component after the first scaling is performed.

In the robotic surgical system according to the first aspect of the present disclosure, as described above, the control device is configured or programmed to perform the first scaling on at least the rotational component of the translational component and the rotational component of the surgical instrument in the received operation amount, and calculate the rotation angle of the joint axis of the robot arm by performing the inverse kinematics calculation on the translational component and the rotational component after the first scaling is performed. The rotational component greatly contributes to the posture of the robot arm, and thus the first scaling is performed on at least the rotational component such that the scaling can be effectively performed on the posture of the robot arm.

A control method of a robotic surgical system that includes a patient-side apparatus including a robot arm having a tip end to which a surgical instrument is attached, an operator-side apparatus including an operation unit to receive an operation amount for the surgical instrument, and a control device configured or programmed to control translation and rotation of the surgical instrument based on the received operation amount according to a second aspect of the present disclosure includes performing scaling on at least a rotational component of a translational component and the rotational component of the surgical instrument in the received operation amount, and calculating a rotation angle of a joint axis of the robot arm by performing an inverse kinematics calculation on the translational component and the rotational component after the scaling is performed.

In the control method of the robotic surgical system according to the second aspect of the present disclosure, as described above, the scaling is performed on at least the rotational component of the translational component and the rotational component of the surgical instrument in the received operation amount. The rotational component greatly contributes to the posture of the robot arm, and thus it is possible to provide the control method of the robotic surgical system capable of effectively scaling the posture of the robot arm by performing the scaling on at least the rotational component.

According to the present disclosure, the posture of the robot arm can be effectively scaled.

The foregoing and other objects, features, aspects and advantages of the present disclosure will become more apparent from the following detailed description of the present disclosure when taken in conjunction with the accompanying drawings.

BRIEF DESCRIPTION OF THE DRAWINGS

FIG. 25 is a diagram for illustrating a control flow of a control device according to the first embodiment.

FIG. 26 is a flowchart for illustrating updating of translation and rotation scaling values according to a second embodiment.

DESCRIPTION OF THE PREFERRED EMBODIMENTS

Figure 1:
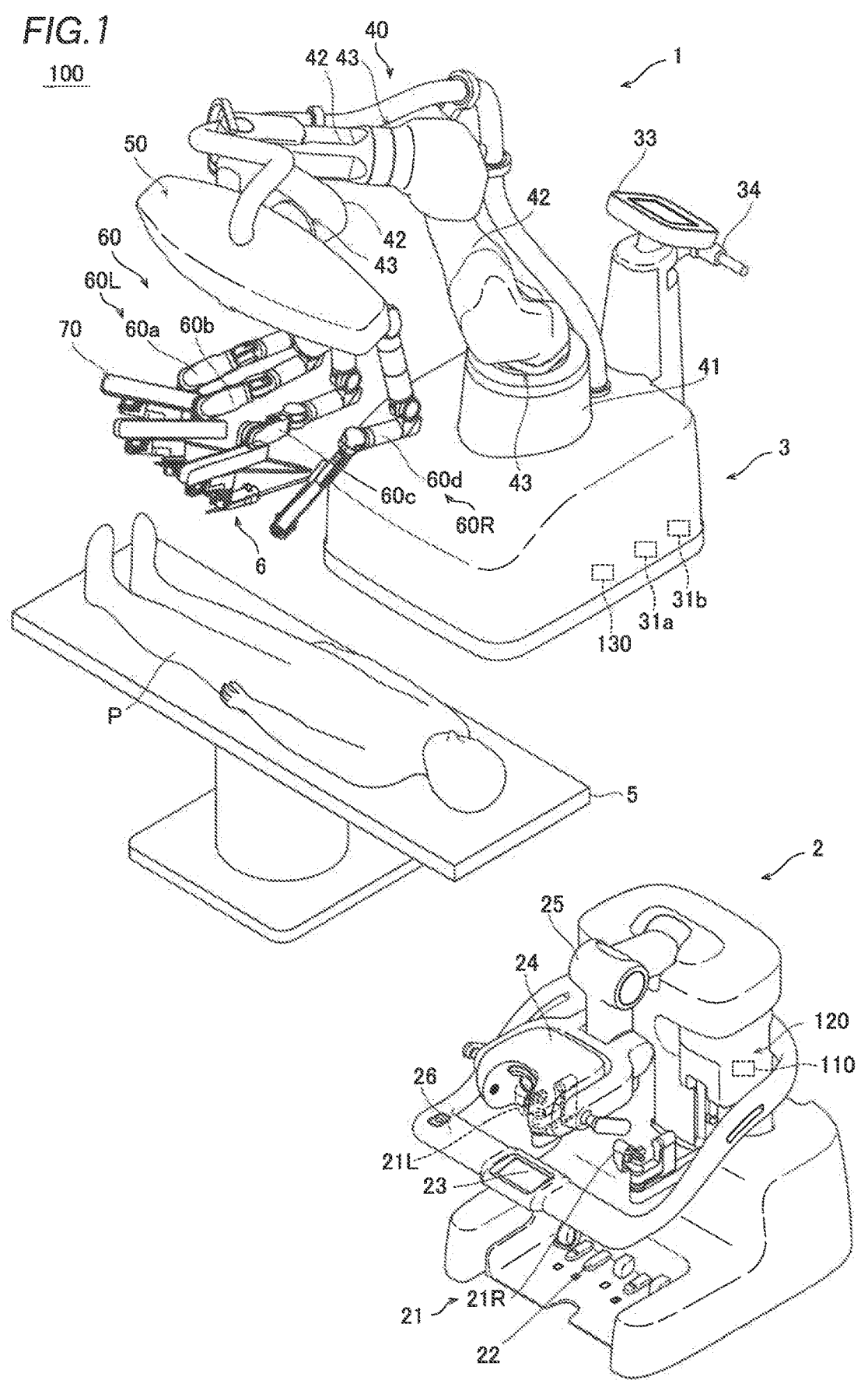
FIG. 1 is a diagram showing the configuration of a robotic surgical system according to a first embodiment.

Embodiments of the present disclosure are hereinafter described with reference to the drawings.

First Embodiment

The configuration of a robotic surgical system 100 according to a first embodiment is now described with reference to FIGS. 1 to 24. The robotic surgical system 100 includes a medical manipulator 1 that is a patient P-side apparatus and a remote control apparatus 2 that is an operator-side apparatus to operate the medical manipulator 1. The medical manipulator 1 includes a medical cart 3 and is movable. The remote control apparatus 2 is spaced apart from the medical manipulator 1, and the medical manipulator 1 is remotely operated by the remote control apparatus 2. An operator such as a doctor inputs a command to the remote control apparatus 2 to cause the medical manipulator 1 to perform a desired operation. The remote control apparatus 2 transmits the input command to the medical manipulator 1. The medical manipulator 1 operates based on the received command. The medical manipulator 1 is arranged in an operating room that is a sterilized sterile field.

The remote control apparatus 2 is arranged inside or outside the operating room, for example. The remote control apparatus 2 includes an operation unit 120 including arms 121 and an operation handle 21 shown in FIG. 3, foot pedals 22, a touch panel 23, a monitor 24, a support arm 25, and a support bar 26. The operation unit 120 includes an operation handle for the operator such as a doctor to input a command.

Figure 3:
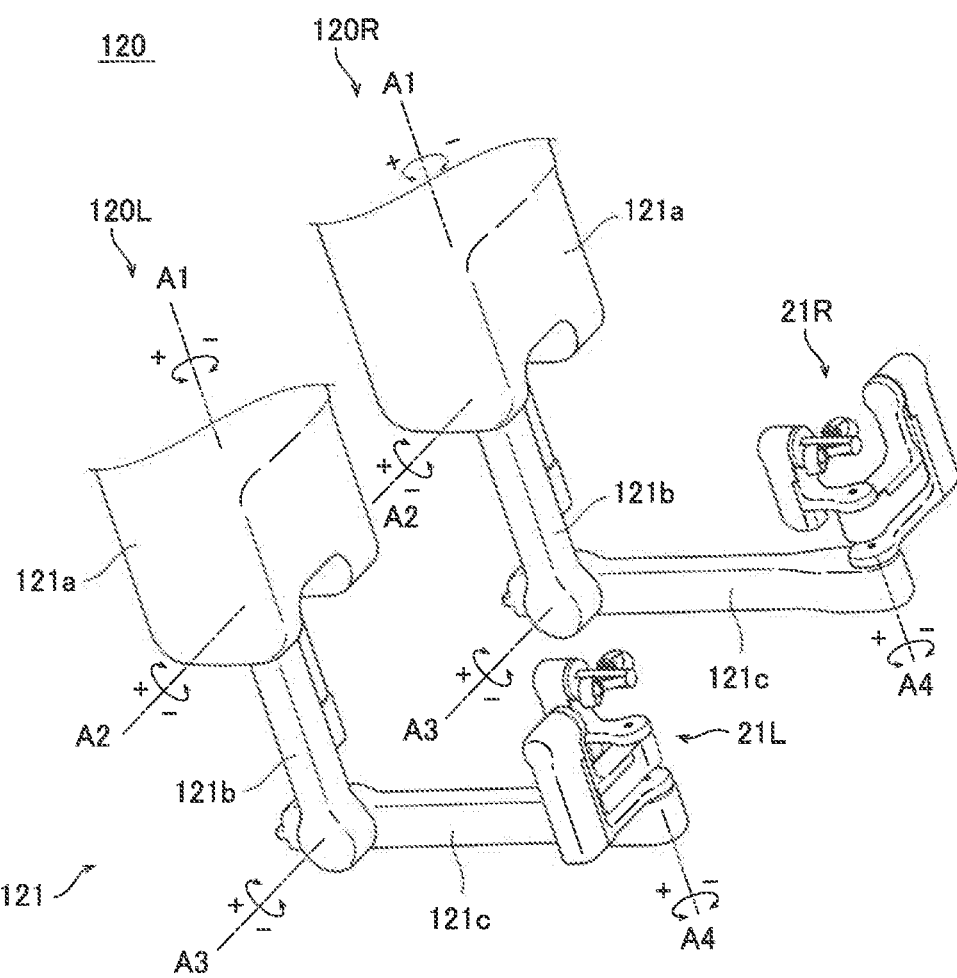
FIG. 3 is a perspective view showing the configuration of an operation unit of a remote control apparatus according to the first embodiment.

As shown in FIG. 3, the operation unit 120 includes an operation unit 120L located on the left side as viewed from the operator such as a doctor and operated by the operator's left hand, and an operation unit 120R located on the right side and operated by the operator's right hand. The configurations of the operation unit 120L and the operation unit 120R are the same as or similar to each other.

The operation unit 120 includes the substantially L-shaped arms 121. The arms 121 each have a first link 121a, a second link 121b, and a third link 121c. The upper end side of the first link 121a is attached to a main body of the remote control apparatus 2 such that the first link 121a is rotatable about an A1 axis along a vertical direction. The upper end side of the second link 121b is attached to the lower end side of the first link 121a such that the second link 121b is rotatable about an A2 axis along a horizontal direction. A first end side of the third link 121c is attached to the lower end side of the second link 121b such that the third link 121c is rotatable about an A3 axis along the horizontal direction. The operation handle 21 is attached to a second end side of the third link 121c such that the operation handle 21 is rotatable about an A4 axis.

The arms 121 each support the operation handle 21 such that the operation handle 21 is movable within a predetermined three-dimensional operation range. Specifically, the arm 121 supports the operation handle 21 such that the operation handle 21 is movable in an upward-downward direction, a right-left direction, and a forward-rearward direction. Robot arms 60 are moved three-dimensionally so as to correspond to three-dimensional operations on the arms 121.

The operation handle 21 operates a surgical instrument 4. Furthermore, the operation handle 21 receives an operation amount for the surgical instrument 4. The operation handle 21 includes an operation handle 21L located on the left side as viewed from the operator such as a doctor and operated by the operator's left hand, and an operation handle 21R located on the right side and operated by the operator's right hand.

Figure 4:
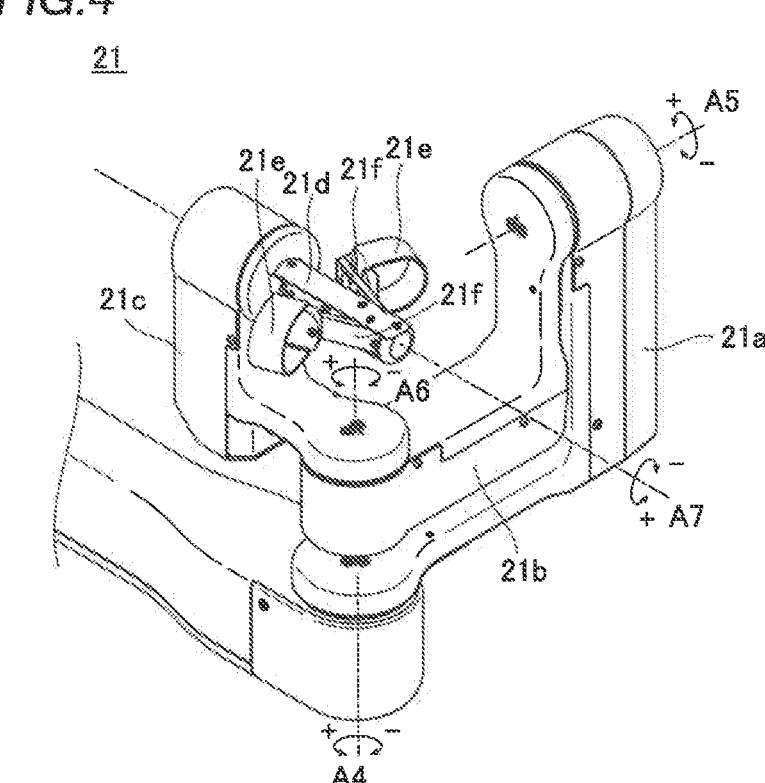
FIG. 4 is a diagram showing the configuration of an operation handle according to the first embodiment.

As shown in FIG. 4, the operation handle 21 includes a link 21a, a link 21b, a link 21c, and a link 21d operated by the operator such as a doctor. The link 21*a* rotates about the A4 axis. The link 21*b* rotates about an A5 axis with respect to the link 21*a*. The link 21*c* rotates about an A6 axis with respect to the link 21*b*. The link 21*d* rotates about an A7 axis with respect to the link 21*c*.

The operation handle 21 includes a pair of grip members 21*f* at the link 21*d*, and cylindrical finger insertion portions 21*e* are provided on the grip members 21*f*. The operator inserts their fingers into a pair of finger insertion portions 21*e* to operate the operation handle 21. Base ends of the pair of grip members 21*f* are rotatably connected to the link 21*d*, and an angle between the pair of grip members 21*f* is increased or decreased such that an opening angle between a jaw member 104*a* and a jaw member 104*b*, which are described below, is changed.

In the operation handle 21, the movement amounts of a robot arm 60 and the surgical instrument 4 are changed with respect to an operation amount received by the operation handle 21. This change is called scaling. For example, when the scale factor of the movement amounts is set to ½, the surgical instrument 4 is controlled to move ½ of the movement distance of the operation handle 21. Thus, fine surgery can be performed accurately.

Figure 5:
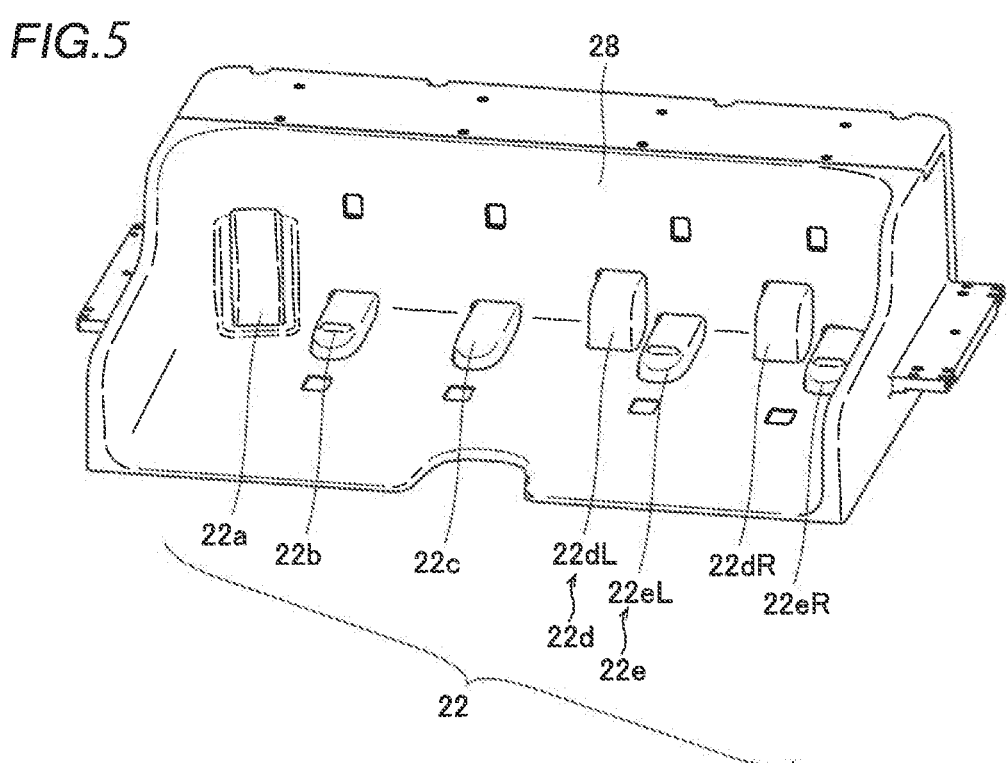
FIG. 5 is a diagram showing the configuration of foot pedals according to the first embodiment.

As shown in FIG. 5, a plurality of foot pedals 22 are provided to perform functions related to the surgical instrument 4. The plurality of foot pedals 22 are arranged on a base 28. The foot pedals 22 include a switching pedal 22*a*, a clutch pedal 22*b*, a camera pedal 22*c*, an incision pedal 22*d*, and a coagulation pedal 22*e*. The switching pedal 22*a*, the clutch pedal 22*b*, the camera pedal 22*c*, the incision pedal 22*d*, and the coagulation pedal 22*e* are operated by the operator's foot. The incision pedal 22*d* includes an incision pedal 22*d* R for a right robot arm 60, and an incision pedal 22*d* L for a left robot arm 60. The coagulation pedal 22*e* includes a coagulation pedal 22*e* R for the right robot arm 60 and a coagulation pedal 22*e* L for the left robot arm 60.

The switching pedal 22*a* switches a robot arm 60 to be operated by the operation handle 21. In the first embodiment, the clutch pedal 22*b* performs a clutch operation to temporarily disconnect an operation connection between the robot arm 60 and the operation handle 21. While the clutch pedal 22*b* is being pressed by the operator, an operation by the operation handle 21 is not transmitted to the robot arms 60. While the camera pedal 22*c* is being pressed by the operator, the operation handle 21 can operate a robot arm 60 to which an endoscope 6 is attached. While the incision pedal 22*d* or the coagulation pedal 22*e* is being pressed by the operator, an electrosurgical device is activated.

As shown in FIG. 1, the monitor 24 is a scope-type display that displays an image captured by the endoscope 6. The support arm 25 supports the monitor 24 so as to align the height of the monitor 24 with the height of the face of the operator such as a doctor. The touch panel 23 is arranged on the support bar 26. The operator's head is detected by a sensor provided in the vicinity of the monitor 24 such that the medical manipulator 1 can be operated by the remote control apparatus 2. The operator operates the operation handle 21 and the foot pedals 22 while visually recognizing an affected area on the monitor 24. Thus, a command is input to the remote control apparatus 2. The command input to the remote control apparatus 2 is transmitted to the medical manipulator 1.

The medical cart 3 includes an input 33. The input 33 receives operations to move a positioner 40, an arm base 50, and a plurality of robot arms 60 or change their postures mainly in order to prepare for surgery before the surgery.

Figure 2:
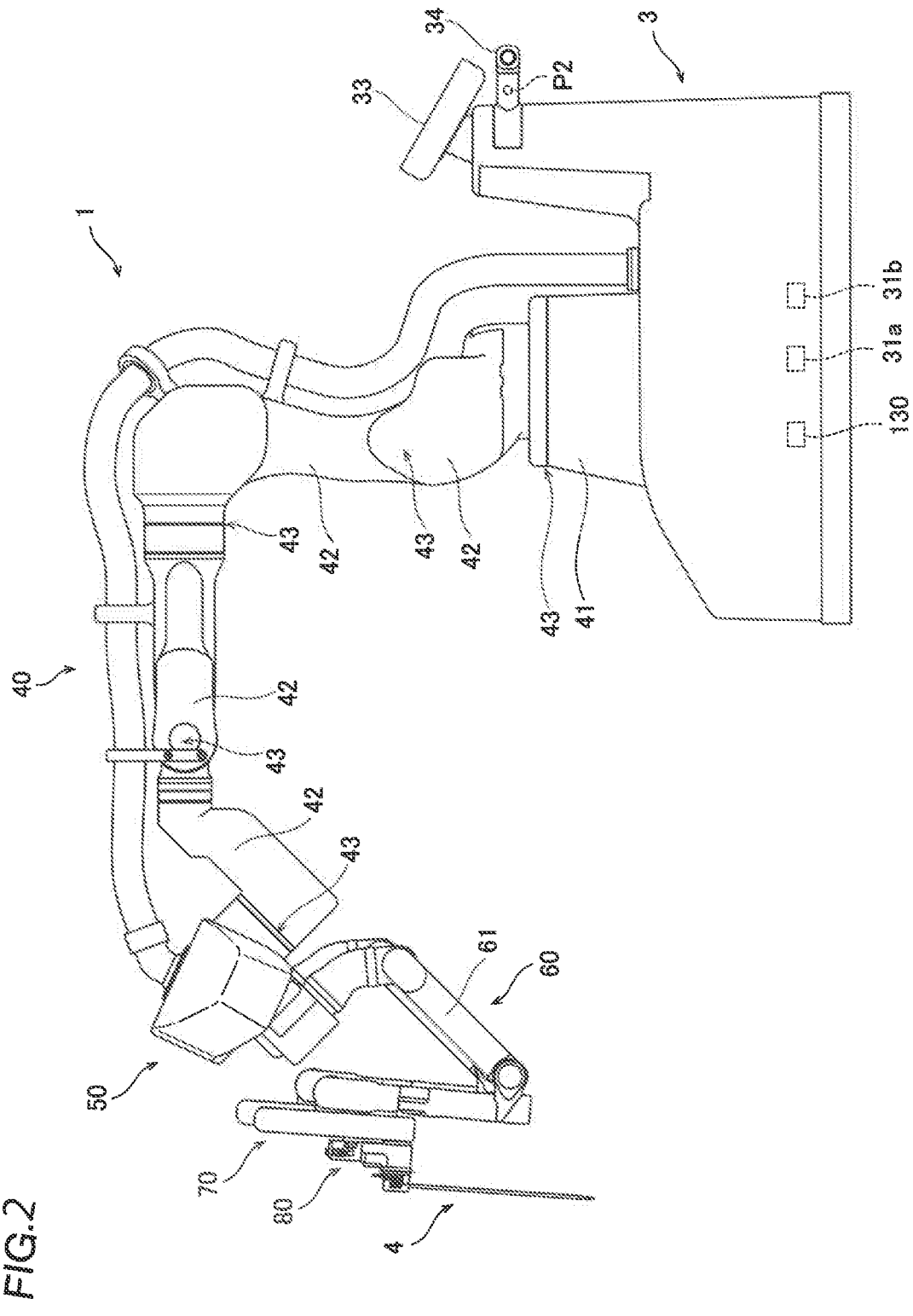
FIG. 2 is a diagram showing the configuration of a medical manipulator according to the first embodiment.

The medical manipulator 1 shown in FIGS. 1 and 2 is arranged in the operating room. The medical manipulator 1 includes the medical cart 3, the positioner 40, the arm base 50, and the plurality of robot arms 60. The arm base 50 is attached to the tip end of the positioner 40. The arm base 50 has a relatively long rod shape. That is, the arm base 50 has a long shape. The bases of the plurality of robot arms 60 are attached to the arm base 50. Each of the plurality of robot arms 60 is able to take a folded and stored posture. The arm base 50 and the plurality of robot arms 60 are covered with sterile drapes and used. The robot arms 60 support surgical instruments 4.

The positioner 40 includes a 7-axis articulated robot, for example. The positioner 40 is arranged on the medical cart 3. The positioner 40 moves the arm base 50. Specifically, the positioner 40 moves the position of the arm base 50 three-dimensionally.

The positioner 40 includes a base 41 and a plurality of links 42 coupled to the base 41. The plurality of links 42 are coupled to each other by joints 43.

As shown in FIG. 1, the surgical instrument 4 is attached to the tip end of each of the plurality of robot arms 60. The surgical instrument 4 includes a replaceable instrument or the endoscope 6 shown in FIG. 10 to capture an image of a surgical site, for example.

Figure 6:
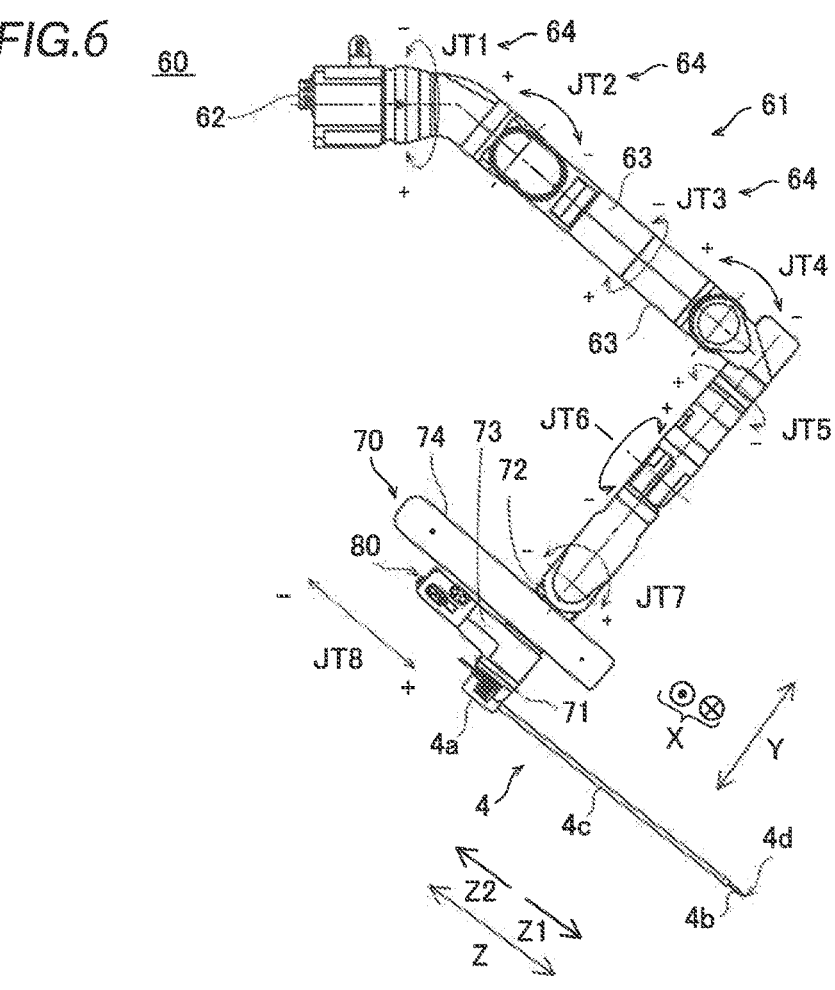
FIG. 6 is a diagram showing the configuration of a robot arm according to the first embodiment.

As shown in FIG. 6, the instrument includes a driven unit 4*a* driven by servomotors M2 provided in a holder 71 of each of the robot arms 60. A pair of forceps 4*b* is provided at the tip end of the instrument. At the tip end of the instrument, in addition to the pair of forceps 4*b*, a pair of scissors, a grasper, a needle holder, a microdissector, a stable applier, a tacker, a suction cleaning tool, a snare wire, a clip applier, etc. are arranged as instruments having joints. At the tip end of the instrument, a cutting blade, a cautery probe, a washer, a catheter, a suction orifice, etc. are arranged as instruments having no joint. The surgical instrument 4 includes a shaft 4*c* that connects the driven unit 4*a* to the pair of forceps 4*b*. The driven unit 4*a*, the shaft 4*c*, and the pair of forceps 4*b* are arranged along a Z direction.

Figure 7:
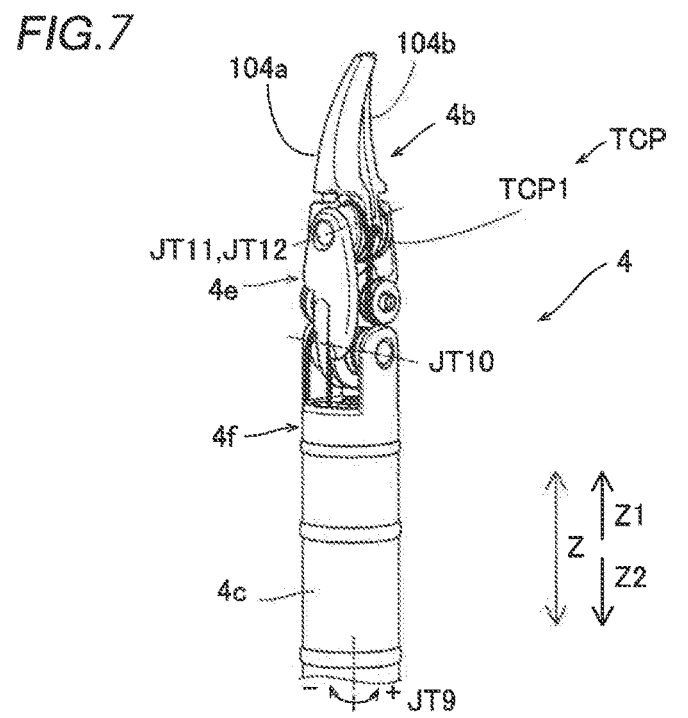
FIG. 7 is a diagram showing a pair of forceps.

As shown in FIG. 7, the instrument includes a first support 4*e* that supports the base end sides of the jaw members 104*a* and 104*b* such that the base end sides of the jaw members 104*a* and 104*b* are rotatable about a JT11 axis on the tip end sides, a second support 4*f* that supports the base end side of the first support 4*e* such that the base end side of the first support 4*e* is rotatable about a JT10 axis on the tip end side, and the shaft 4*c* connected to the base end side of the second support 4*f*. The driven unit 4*a*, the shaft 4*c*, the second support 4*f*, the first support 4*e*, and the pair of forceps 4*b* are arranged along the Z direction. The JT11 axis is orthogonal to the Z direction in which the shaft 4*c* extends. The JT10 axis is spaced apart from the JT11 axis in the direction in which the shaft 4*c* extends, and is orthogonal to the direction in which the shaft 4*c* extends and the JT11 axis. The JT10 axis is an example of a wrist joint that bends a jaw provided on a distal end side of the shaft 4*c*.

The pair of forceps 4*b* is attached to the first support 4*e* so as to rotate about the JT11 axis. The second support 4*f* supports the first support 4*e* such that the first support 4*e* is rotatable about the JT10 axis. That is, the first support 4*e* is attached to the second support 4*f* so as to rotate about the JT10 axis. A portion of the first support 4*e* on the Z1 direction side, which is the tip end side, has a U-shape. TCP1 is set as a tool center point at the center of the tip end of the U-shaped portion of the first support 4*e* in the JT11 axis.

The pair of forceps 4*b* as the surgical instrument 4 includes a JT9 axis as a rotation axis of the shaft 4*c* and a JT12 axis as an opening/closing axis of the jaw members 104a and 104b. The rotation axis of the shaft 4c is an axis along the direction in which the shaft 4c extends. A plurality of servomotors M2 are provided in the holder 71 of the robot arm 60, and rotary bodies of the driven unit 4a are driven by the plurality of servomotors M2. Thus, the surgical instrument 4 is driven around the JT9 axis to the JT12 axis. For example, four servomotors M2 are provided.

Figure 10:
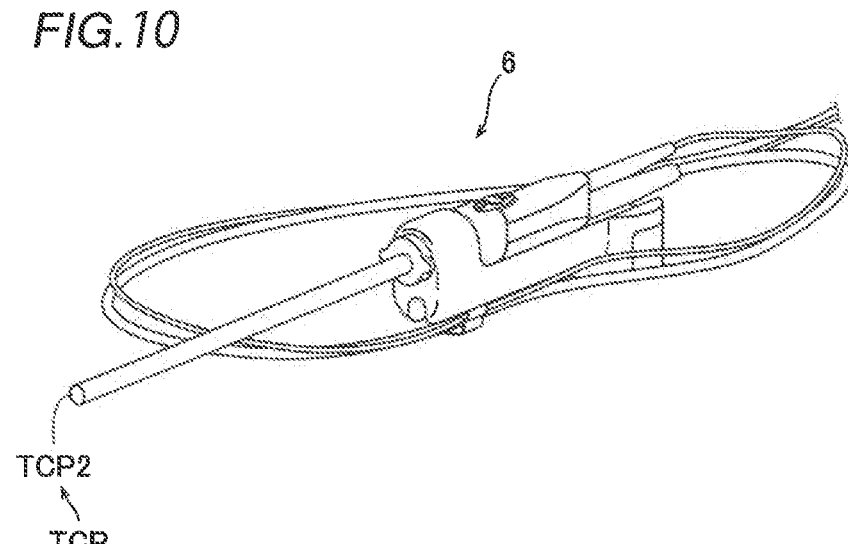
FIG. 10 is a diagram showing an endoscope.

As shown in FIG. 10, TCP2 of the endoscope 6 is set at the tip end of the endoscope 6.

Figure 8:
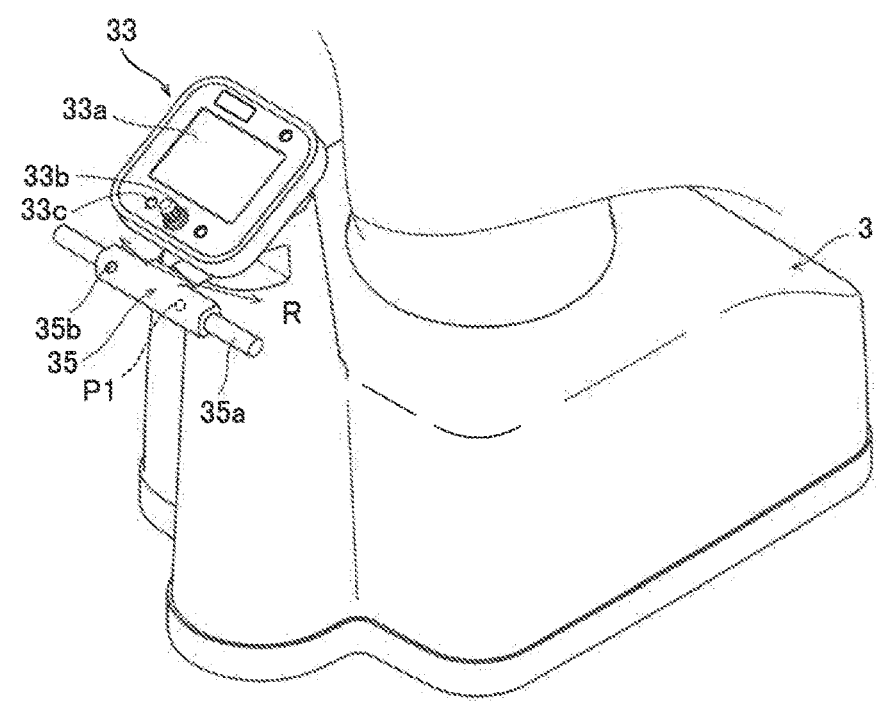
FIG. 8 is a perspective view showing the configuration of a medical cart according to the first embodiment.

As shown in FIG. 8, a display 33a is provided on the medical cart 3. The display 33a is arranged on the input 33 of the medical cart 3. A joystick 33b for operating movement of the positioner 40 is provided in the vicinity of the display 33a of the medical cart 3. The positioner 40 can be operated three-dimensionally by selecting an operation mode displayed on the display 33a and operating the joystick 33b. At the time of roll-in, the joystick 33b is operated such that the positioner 40 is moved so as to move the arm base 50 on a two-dimensional plane.

In the vicinity of the joystick 33b of the medical cart 3, an enable switch 33c is provided to enable or disable movement of the positioner 40. The joystick 33b is operated while the enable switch 33c is being pressed to enable movement of the positioner 40 such that the positioner 40 is moved. Specifically, the enable switch 33c is arranged below the display 33a and adjacent to the joystick 33b on the input 33.

The medical cart 3 includes an operation handle 35 to receive an operator's steering operation. The medical cart 3 moves a robot main body 1a based on the received steering operation. The operation handle 35 is arranged in the vicinity of the display 33a of the medical cart 3. The operation handle 35 includes a throttle 35a that is gripped and rotated by an operator such as a nurse or a technician to operate movement of the medical cart 3. Specifically, the operation handle 35 is arranged below the input 33. The throttle 35a is arranged on one side of the operation handle 35. The throttle 35a is rotated from the front side to the rear side such that the medical cart 3 moves forward. The throttle 35a is rotated from the rear side to the front side such that the medical cart 3 moves rearward. The speed of the medical cart 3 is changed according to the amount of rotation of the throttle 35a. The operation handle 35 is rotatable to the left and right shown as an R direction, and the medical cart 3 is turned with rotation of the operation handle 35.

An enable switch 35b is provided to enable or disable movement of the medical cart 3 on the operation handle 35 of the medical cart 3. The throttle 35a of the operation handle 35 is operated while the enable switch 35b is being pressed to enable movement of the medical cart 3 such that the medical cart 3 is moved.

The configuration of the robot arms 60 is now described in detail.

As shown in FIG. 6, each of the robot arms 60 includes an arm portion 61 and a translation mechanism 70 provided at the tip end of the arm portion 61. The arm portion 61 includes a base 62, links 63, and joints 64. The translation mechanism 70 includes a base end side link 72 connected to the tip end of the arm portion 61, a tip end side link 73, and a coupling link 74 provided between the base end side link 72 and the tip end side link 73. The tip end sides of the robot arms 60 three-dimensionally move with respect to the arm base 50 on the base sides of the robot arms 60. The arm portion 61 includes a 7-axis articulated robot arm. The plurality of robot arms 60 have the same or similar configuration as each other.

Figure 15:
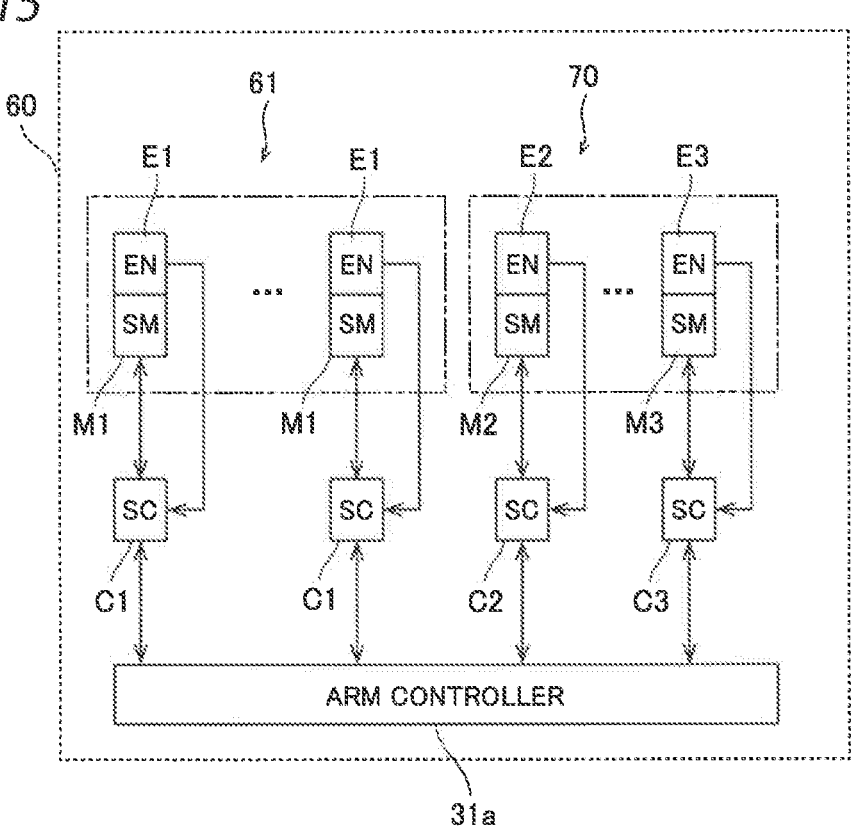
FIG. 15 is a control block diagram of the robot arm according to the first embodiment.

As shown in FIG. 6, the robot arms 60 each include JT1 to JT7 axes as rotation axes and a JT8 axis as a linear motion axis. The JT1 to JT7 axes correspond to the rotation axes of the joints 64 of the arm portion 61. The JT7 axis corresponds to a base end side link 72 of the translation mechanism 70. The JT8 axis corresponds to an axis that moves a tip end side link 73 of the translation mechanism 70 relative to the base end side link 72 along the Z direction. That is, servomotors M1 shown in FIG. 15 are provided so as to correspond to the JT1 to JT7 axes of the robot arm 60. Furthermore, a servomotor M3 is provided so as to correspond to the JT8 axis.

The translation mechanism 70 is provided at the tip end of the arm portion 61, and the surgical instrument 4 is attached thereto. The translation mechanism 70 translates the surgical instrument 4 in a direction in which the surgical instrument 4 is inserted into the patient P. Furthermore, the translation mechanism 70 translates the surgical instrument 4 relative to the arm portion 61. Specifically, the translation mechanism 70 includes the holder 71 that holds the surgical instrument 4. The servomotors M2 shown in FIG. 15 are housed in the holder 71.

Figure 9:
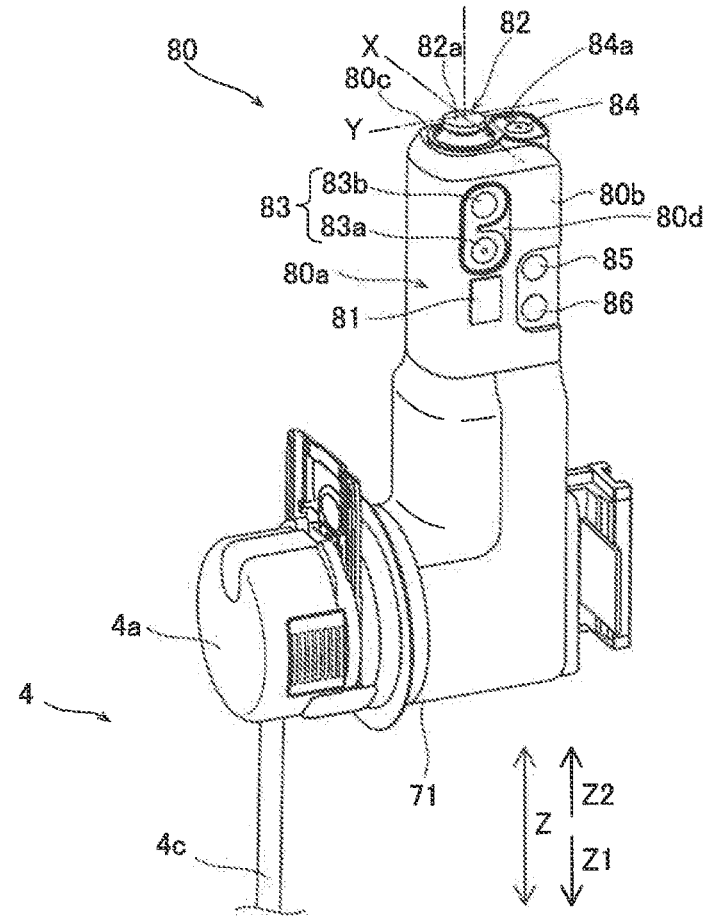
FIG. 9 is a perspective view showing the configuration of an arm operation unit of the medical manipulator according to the first embodiment.

As shown in FIG. 9, the medical manipulator 1 includes an arm operation unit 80 attached to each of the robot arms 60 to operate the robot arm 60. The arm operation unit 80 includes an enable switch 81, a joystick 82, and a switch unit 83. The enable switch 81 enables or disables movement of the robot arm 60 in response to the joystick 82 and the switch unit 83. The enable switch 81 enables movement of the surgical instrument 4 by the robot arm 60 when the enable switch 81 is pressed by an operator such as a nurse or an assistant grasping the arm operation unit 80.

The switch unit 83 includes a switch 83a to move the surgical instrument 4 in the direction in which the surgical instrument 4 is inserted into the patient P, along the longitudinal direction of the surgical instrument 4, and a switch 83b to move the surgical instrument 4 in a direction opposite to the direction in which the surgical instrument 4 is inserted into the patient P. Both the switch 83a and the switch 83b are push-button switches.

Figure 11:
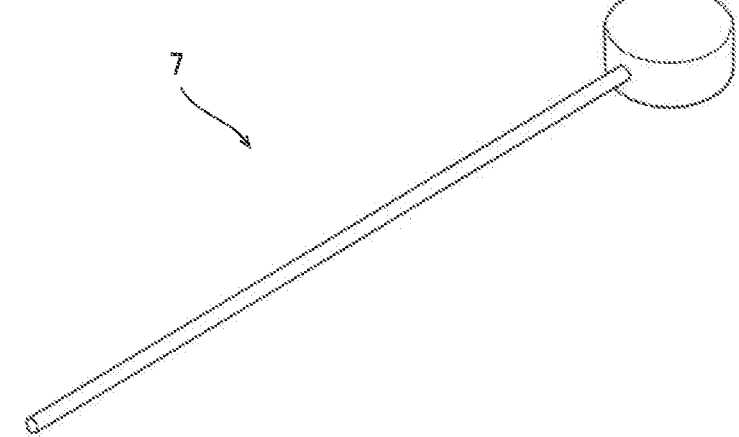
FIG. 11 is a diagram showing a pivot position setting instrument.
Figures 12, 13:
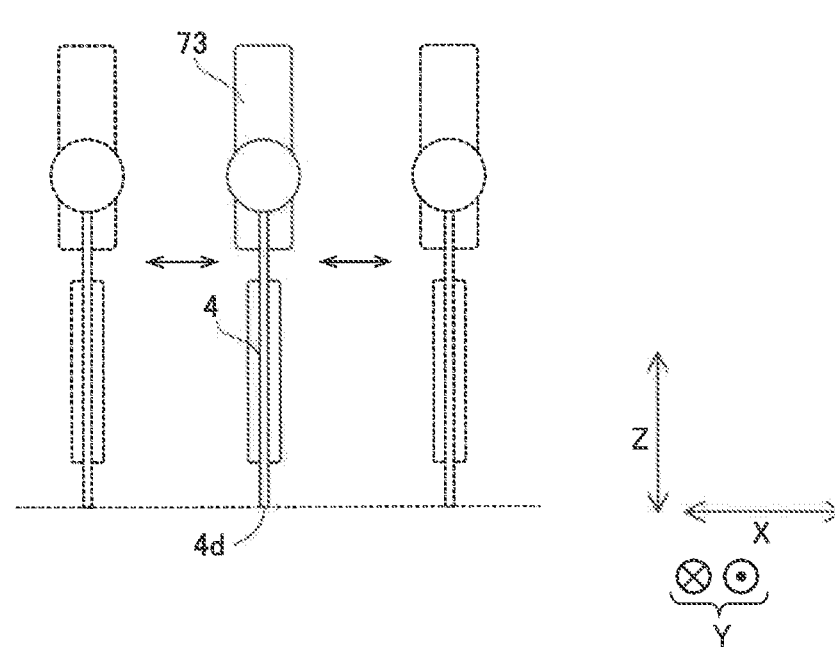
FIG. 12 is a diagram for illustrating translation of the robot arm.
FIG. 13 is a diagram for illustrating rotation of the robot arm.

As shown in FIG. 9, the arm operation unit 80 includes a pivot button 85 to set a pivot position PP that serves as a fulcrum shown in FIG. 13 for movement of the surgical instrument 4 attached to the robot arm 60. The pivot button 85 is provided adjacent to the enable switch 81 on a surface 80b of the arm operation unit 80. The pivot button 85 is pressed when the tip end of the endoscope 6 shown in FIG. 10 or a pivot position setting instrument 7 shown in FIG. 11 is located at a position corresponding to the insertion position of a trocar T inserted into the body surface S of the patient P such that the pivot position PP is set and stored in a storage 32. In the setting of the pivot position PP, the pivot position PP is set as one point, and the direction of the surgical instrument 4 is not set.

As shown in FIG. 1, the endoscope 6 is attached to the tip end of one (robot arm 60c, for example) of the plurality of robot arms 60, and the surgical instruments 4 other than the endoscope 6 are attached to the tip ends of the remaining robot arms 60a, 60b, and 60d, for example. Specifically, in surgery, the endoscope 6 is attached to one of four robot arms 60, and the surgical instruments 4 such as pairs of forceps 4b other than the endoscope 6 are attached to the three robot arms 60. The pivot position PP is set with the endoscope 6 attached to the robot arm 60 to which the endoscope 6 is to be attached. Furthermore, pivot positions PP are set with pivot position setting instruments 7 attached to the robot arms 60 to which the surgical instruments 4 other than the endoscope 6 are to be attached. The endoscope 6 is attached to one of two robot arms 60b and 60c arranged in the center among the four robot arms 60 arranged adjacent to each other. That is, the pivot position PP is individually set for each of the plurality of robot arms 60. The robot arm 60c is an example of a second robot arm.

As shown in FIG. 9, an adjustment button 86 for optimizing the position of the robot arm 60 is provided on the surface 80b of the arm operation unit 80. After the pivot position PP for the robot arm 60 to which the endoscope 6 has been attached is set, the adjustment button 86 is pressed such that the positions of the other robot arms 60 and the arm base 50 are optimized.

As shown in FIG. 9, the arm operation unit 80 includes a mode switching button 84 to switch between a mode for translating the surgical instrument 4 attached to the robot arm 60 as shown in FIG. 12 and a mode for rotationally moving the surgical instrument 4 attached to the robot arm 60 as shown in FIG. 13. Furthermore, a mode indicator 84a is provided in the vicinity of the mode switching button 84. The mode indicator 84a indicates a switched mode. Specifically, the mode indicator 84a is turned on to indicate a rotational movement mode and is turned off to indicate a translational mode.

The mode indicator 84a also serves as a pivot position indicator that indicates that the pivot position PP has been set.

As shown in FIG. 12, in the mode for translating the robot arm 60, the robot arm 60 is moved such that the tip end 4d of the surgical instrument 4 moves on an X-Y plane. As shown in FIG. 13, in the mode for rotationally moving the robot arm 60, when the pivot position PP is not set, the robot arm 60 is moved such that the surgical instrument 4 rotationally moves about the pair of forceps 4b, and when the pivot position PP is set, the robot arm 60 is moved such that the surgical instrument 4 rotationally moves about the pivot position PP as a fulcrum. The surgical instrument 4 is rotationally moved while the shaft 4c of the surgical instrument 4 is inserted into the trocar T.

Figure 14:
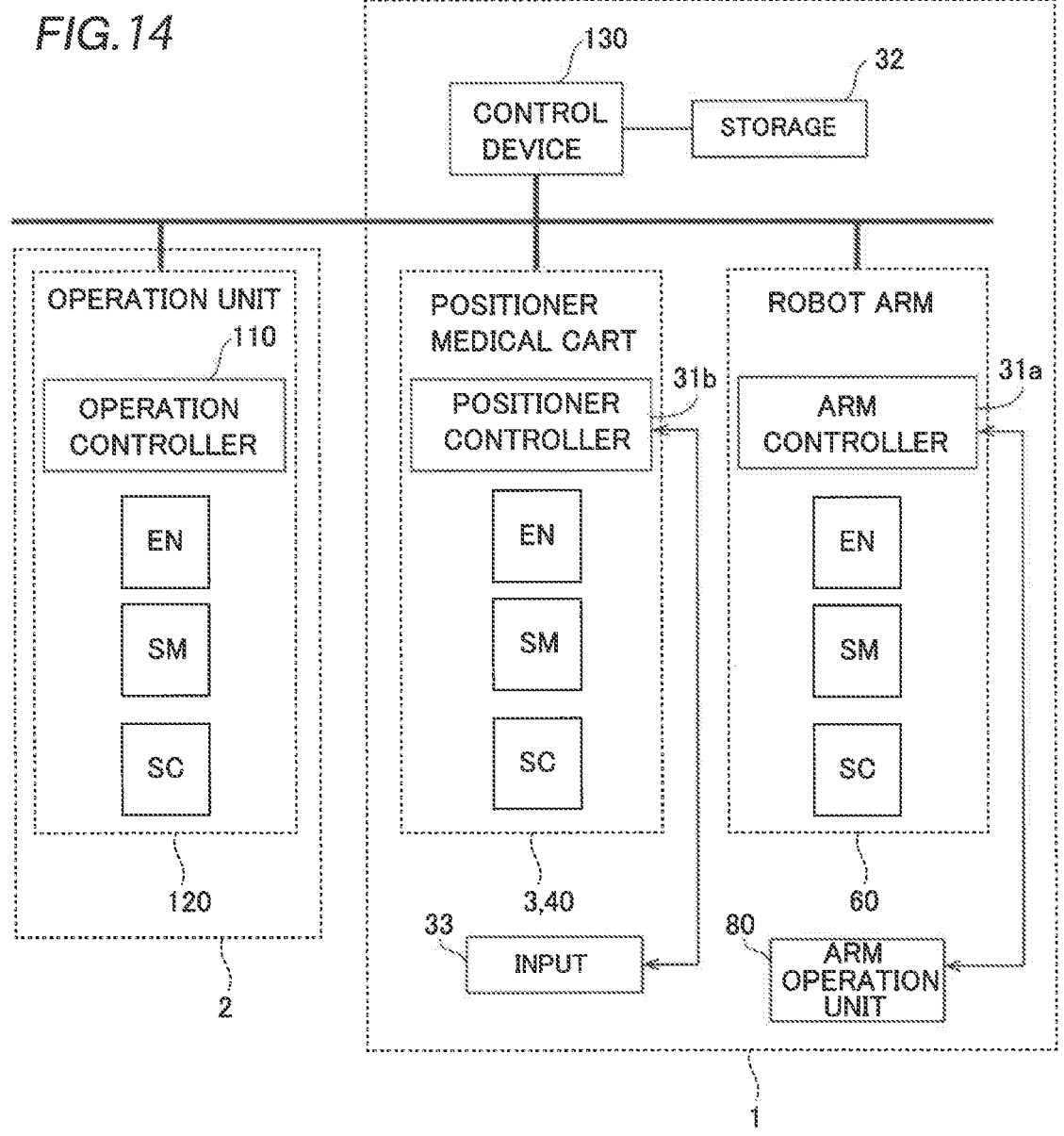
FIG. 14 is a control block diagram of the medical manipulator according to the first embodiment.

As shown in FIG. 14, the robotic surgical system 100 includes a control device 130 that controls the entire robotic surgical system 100. The control device 130 is arranged inside the medical manipulator 1. An arm controller 31a that controls the robot arm 60 is arranged in the medical manipulator 1. The arm controller 31a is arranged so as to correspond to each of the plurality of robot arms 60. A positioner controller 31b that controls the positioner 40 and the medical cart 3 is arranged in the medical cart 3. An operation controller 110 that controls the operation unit 120 is arranged in the operation unit 120. The operation controller 110 is arranged in each of the operation unit 120L and the operation unit 120R. The control device 130 communicates with each of the positioner controller 31b, the arm controller 31a, and the operation controller 110. The control device 130 controls each of the positioner controller 31b, the arm controller 31a, and the operation controller 110.

As shown in FIG. 15, the arm portion 61 includes a plurality of servomotors M1, encoders E1, and speed reducers so as to correspond to a plurality of joints 64 of the arm portion 61. The encoders E1 detect the rotation angles of the servomotors M1. The speed reducers slow down rotation of the servomotors M1 to increase the torques.

In the robot arm 60, servo controllers C1 that control servomotors M1 are arranged. The encoders E1 that detect the rotation angles of the servomotors M1 are electrically connected to the servo controllers C1.

As shown in FIG. 15, the translation mechanism 70 includes the servomotors M2 to rotate the rotary bodies provided in the driven unit 4a of the surgical instrument 4, the servomotor M3 to translate the surgical instrument 4, encoders E2 and E3, and speed reducers. The encoders E2 and E3 detect the rotation angles of the servomotors M2 and M3, respectively. The speed reducers slow down rotation of the servomotors M2 and M3 to increase the torques.

In the robot arm 60, servo controllers C2 that control the servomotors M2 to drive the surgical instrument 4 are arranged. The encoders E2 that detect the rotation angles of the servomotors M2 are electrically connected to the servo controllers C2. Furthermore, in the robot arm 60, a servo controller C3 that controls the servomotor M3 to translate the translation mechanism 70 is arranged. The encoder E3 that detects the rotation angle of the servomotor M3 is electrically connected to the servo controller C3.

The operation amount received by the operation unit 120 of the remote control apparatus 2 is input to the control device 130 via the operation controller 110. The control device 130 generates position commands for driving the robot arm 60 and the surgical instrument 4 based on the received operation amount and the rotation angles detected by the encoders E1 to E3. The generated position commands are input to the servo controllers C1 to C3 via the arm controller 31a. The servo controllers C1 to C3 generate current commands based on the position commands input from the control device 130 via the arm controller 31a and the rotation angles detected by the encoders E1 to E3, and output the current commands to the servomotors M1 to M3. Thus, the robot arm 60 is moved according to the operation received by the operation unit 120 of the remote control apparatus 2.

As shown in FIG. 14, the control device 130 operates the robot arm 60 based on an operation received by the joystick 82 of the arm operation unit 80. Specifically, the arm controller 31a outputs an input signal input from the joystick 82 to the control device 130. The control device 130 generates position commands based on the received input signal and the rotation angles detected by the encoders E1, and outputs the position commands to the servo controllers C1 via the arm controller 31a. The servo controllers C1 generate current commands based on the position commands input from the arm controller 31a and the rotation angles detected by the encoders E1, and output the current commands to the servomotors M1. Thus, the robot arm 60 is moved according to an operation command input to the joystick 82.

The control device 130 operates the robot arm 60 based on an input signal from the switch unit 83 of the arm operation unit 80. Specifically, the arm controller 31a outputs the input signal input from the switch unit 83 to the control device 130. The control device 130 generates a position command based on the received input signal and the rotation angle detected by the encoder E1 or E3, and outputs the position command to the servo controller C1 or C3 via the arm controller 31a. The servo controller C1 or C3 generates a current command based on the position command input from the arm controller 31a and the rotation angle detected by the encoder E1 or E3, and outputs the current command to the servomotor M1 or M3. Thus, the robot arm 60 is moved according to an operation command input to the switch unit 83.

Figure 16:
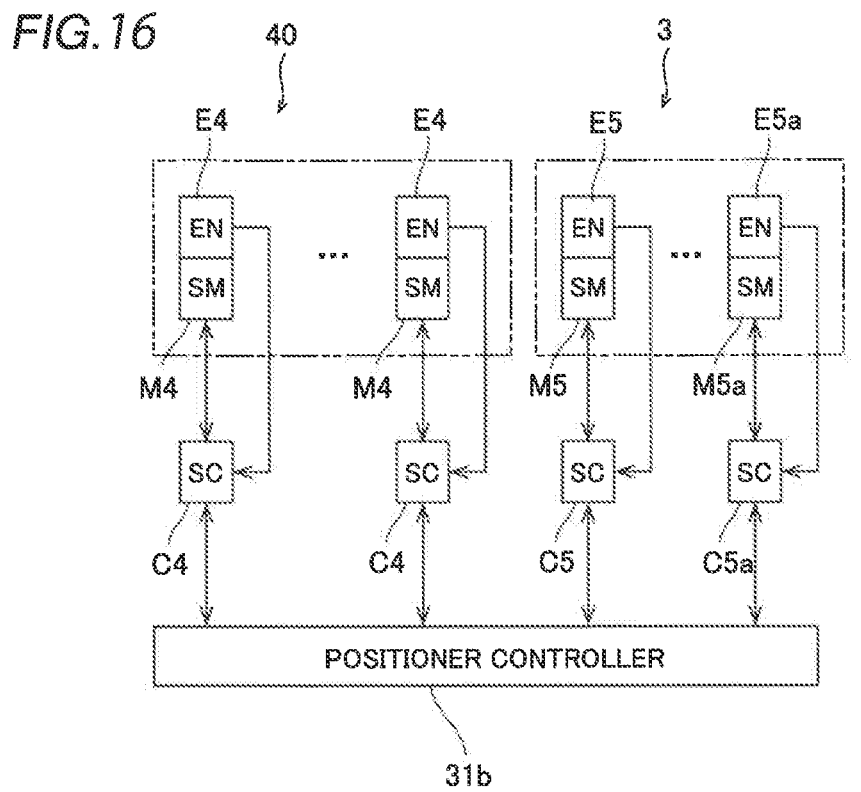
FIG. 16 is a control block diagram of the medical cart and a positioner according to the first embodiment.

As shown in FIG. 16, the positioner 40 includes a plurality of servomotors M4, encoders E4, and speed reducers so as to correspond to a plurality of joints 43 of the positioner 40. The encoders E4 detect the rotation angles of the servomotors M4. The speed reducers slow down rotation of the servomotors M4 to increase the torques.

The medical cart 3 includes front wheels as drive wheels and rear wheels steered by the operation handle 35. The rear wheels are arranged closer to the operation handle 35 than the front wheels. Furthermore, the medical cart 3 includes servomotors M5 to drive a plurality of front wheels of the medical cart 3, respectively, encoders E5, speed reducers, and brakes. The speed reducers slow down rotation of the servomotors M5 to increase the torques. Furthermore, a potentiometer P1 shown in FIG. 8 is provided on the operation handle 35 of the medical cart 3, and the servomotors M5 of the front wheels are driven based on a rotation angle detected by the potentiometer P1 according to the twist of the throttle 35a. The rear wheels of the medical cart 3 are of the dual wheel type, and the rear wheels are steered based on the rightward-leftward operation of the operation handle 35. Furthermore, a potentiometer P2 shown in FIG. 2 is provided on the operation handle 35 of the medical cart 3, and servomotors M5a, encoders E5a, and speed reducers are provided on the rear wheels of the medical cart 3. The speed reducers slow down rotation of the servomotors M5a to increase the torques. The servomotors M5a are driven based on a rotation angle detected by the potentiometer P2 according to the rightward-leftward operation of the operation handle 35. That is, steering of the rear wheels by the rightward-leftward operation of the operation handle 35 is power-assisted by the servomotors M5a.

The medical cart 3 moves in the forward-rearward direction by driving the front wheels. Furthermore, the operation handle 35 of the medical cart 3 is rotated such that the rear wheels are steered, and the medical cart 3 moves in a rightward-leftward direction.

As shown in FIG. 16, in the positioner 40, servo controllers C4 that controls the servomotors M4 to move the positioner 40 are arranged. The encoders E4 that detect the rotation angles of the servomotors M4 are electrically connected to the servo controllers C4. In the medical cart 3, servo controllers C5 that control the servomotors M5 to drive the front wheels of the medical cart 3 are arranged. The encoders E5 that detect the rotation angles of the servomotors M5 are electrically connected to the servo controllers C5. In the medical manipulator 1, servo controllers C5a that control the servomotors M5a to power-assist steering of the rear wheels of the medical cart 3 are arranged. The encoders E5a that detect the rotation angles of the servomotors M5a are electrically connected to the servo controllers C5a.

As shown in FIG. 14, operation information related to setting of a preparation position, for example, is input from the input 33 to the control device 130 via the positioner controller 31b. The control device 130 generates position commands based on the operation information input from the input 33 and the rotation angles detected by the encoders E4, and outputs the position commands to the servo controllers C4 via the positioner controller 31b. The servo controllers C4 generate current commands based on the position commands input from the positioner controller 31b and the rotation angles detected by the encoders E4, and output the current commands to the servomotors M4. Thus, the positioner 40 is moved according to an operation command input to the input 33. Similarly, the control device 130 moves the medical cart 3 based on operation information from the input 33.

Figure 17:
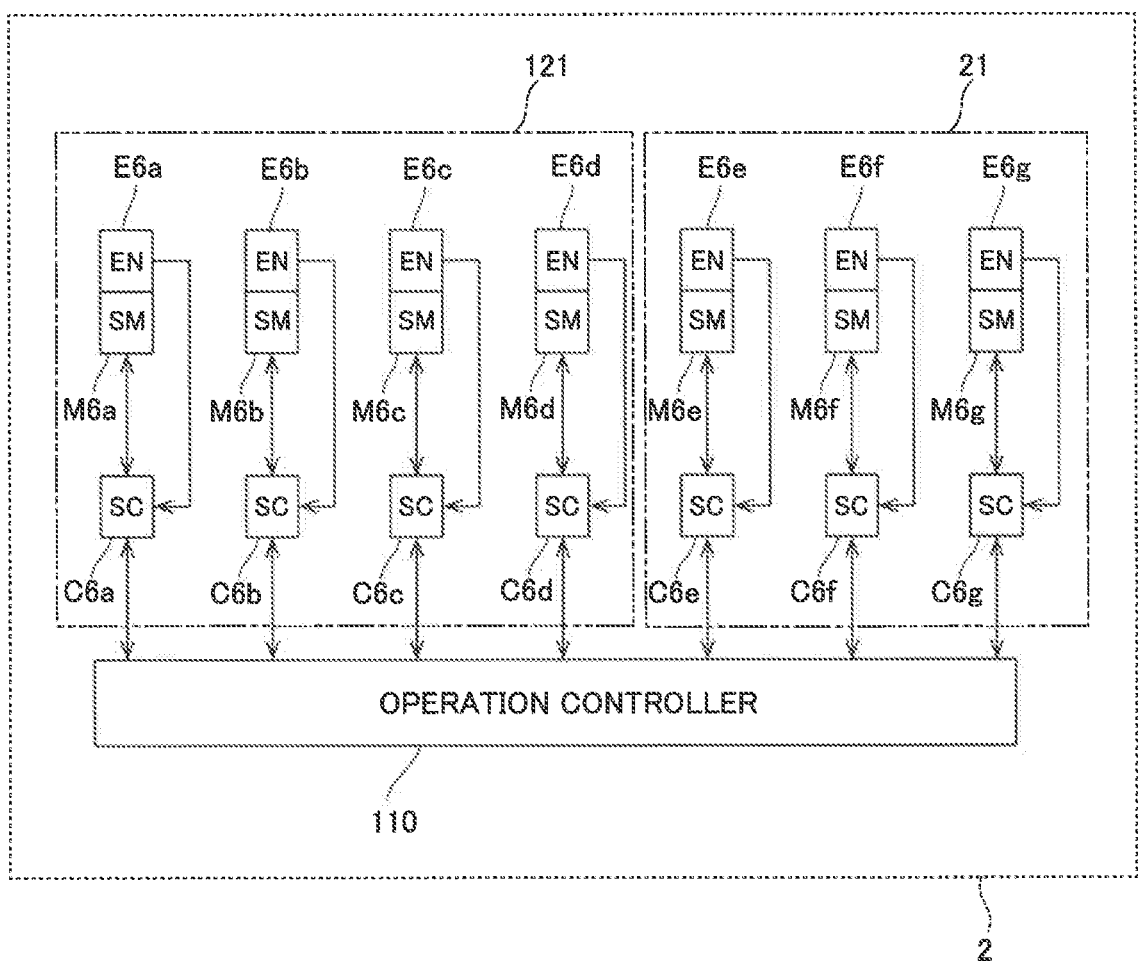
FIG. 17 is a control block diagram of the operation unit of the remote control apparatus according to the first embodiment.

As shown in FIG. 17, the remote control apparatus 2 includes the operation controller 110. In the operation unit 120, servo controllers C6a to C6g that control servomotors M6a to M6g provided so as to correspond to the axes A1 to A7, which are the rotation axes of the operation unit 120 including the arms 121 and the operation handle 21, are arranged. Furthermore, encoders E6a to E6g that detect the rotation angles of the servomotors M6a to M6g are electrically connected to the servo controllers C6a to C6g. The servomotors M6a to M6g, the servo controllers C6a to C6g, and the encoders E6a to E6g are provided in each of the operation unit 120L and the operation unit 120R.

The control device 130 controls the servomotors M6a to M6g to generate torques that cancel gravitational torques generated on the rotation axes A1 to A7 of the servomotors M6a to M6g according to the posture of the operation unit 120. Thus, the operator can operate the operation unit 120 with a relatively small force.

The control device 130 generates torques on the rotation axes A1 to A7 of the servomotors M6a to M6g according to an operation on the operation unit 120 via the operation controller 110, and controls the servomotors M6a to M6g to assist the operation of the operator. Thus, the operator can operate the operation unit 120 with a relatively small force.

Figure 18:
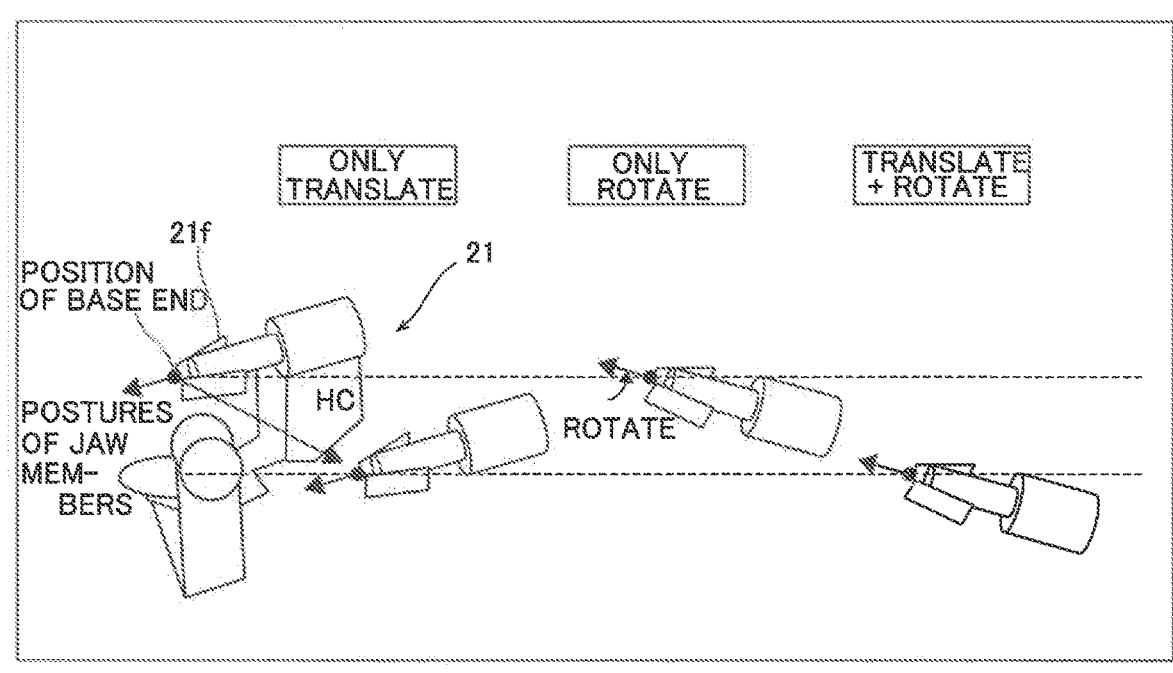
FIG. 18 is a diagram for illustrating translation and rotation of the operation handle.
Figure 19:
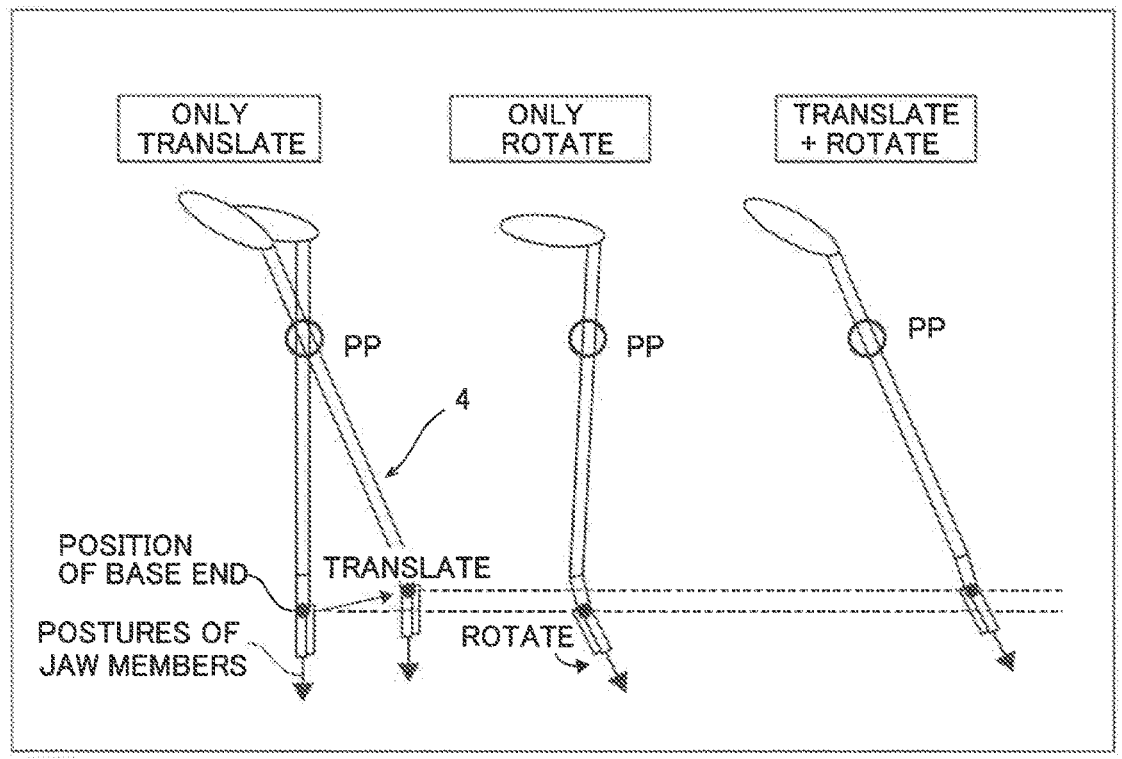
FIG. 19 is a diagram for illustrating translation and rotation of a surgical instrument.

When the operator inserts their fingers into the pair of finger insertion portions 21e of the grip members 21f and translates the operation handle 21 as shown in a left figure of FIG. 18, the surgical instrument 4 translates as shown in a left figure of FIG. 19. That is, the postures of the jaw member 104a and the jaw member 104b do not change, but the position of the base end of the jaw member 104a and the jaw member 104b is translated. The position of the base end refers to the JT11 axis. Furthermore, the jaw member 104a and the jaw member 104b translate with the pivot position PP as a fulcrum. The robot arm 60 and the shaft 4c move such that the jaw member 104a and the jaw member 104b translate with the pivot position PP as a fulcrum.

When the operator inserts their fingers into the pair of finger insertion portions 21e of the grip members 21f and rotationally moves the operation handle 21 as shown in a center figure of FIG. 18, the jaw member 104a and the jaw member 104b of the surgical instrument 4 rotate as shown in a center figure of FIG. 19. Furthermore, the jaw member 104a and the jaw member 104b rotate with the pivot position PP as a fulcrum. The robot arm 60 and the shaft 4c move such that the jaw member 104a and the jaw member 104b rotate with the pivot position PP as a fulcrum.

As shown in a right figure of FIG. 18 and a right figure of FIG. 19, both translation and rotation may be performed by one operation.

A control performed by the control device 130 when the operation unit 120 receives an operation of the operator is now described. The control of the control device 130 described below is performed similarly on any of the robot arm 60c having a tip end to which the endoscope 6 is attached, and the robot arms 60a, 60b, and 60d having tip ends to which the surgical instruments 4 other than the endoscope 6 are attached. Driving of the surgical instruments 4 is similarly performed.

Figure 20:
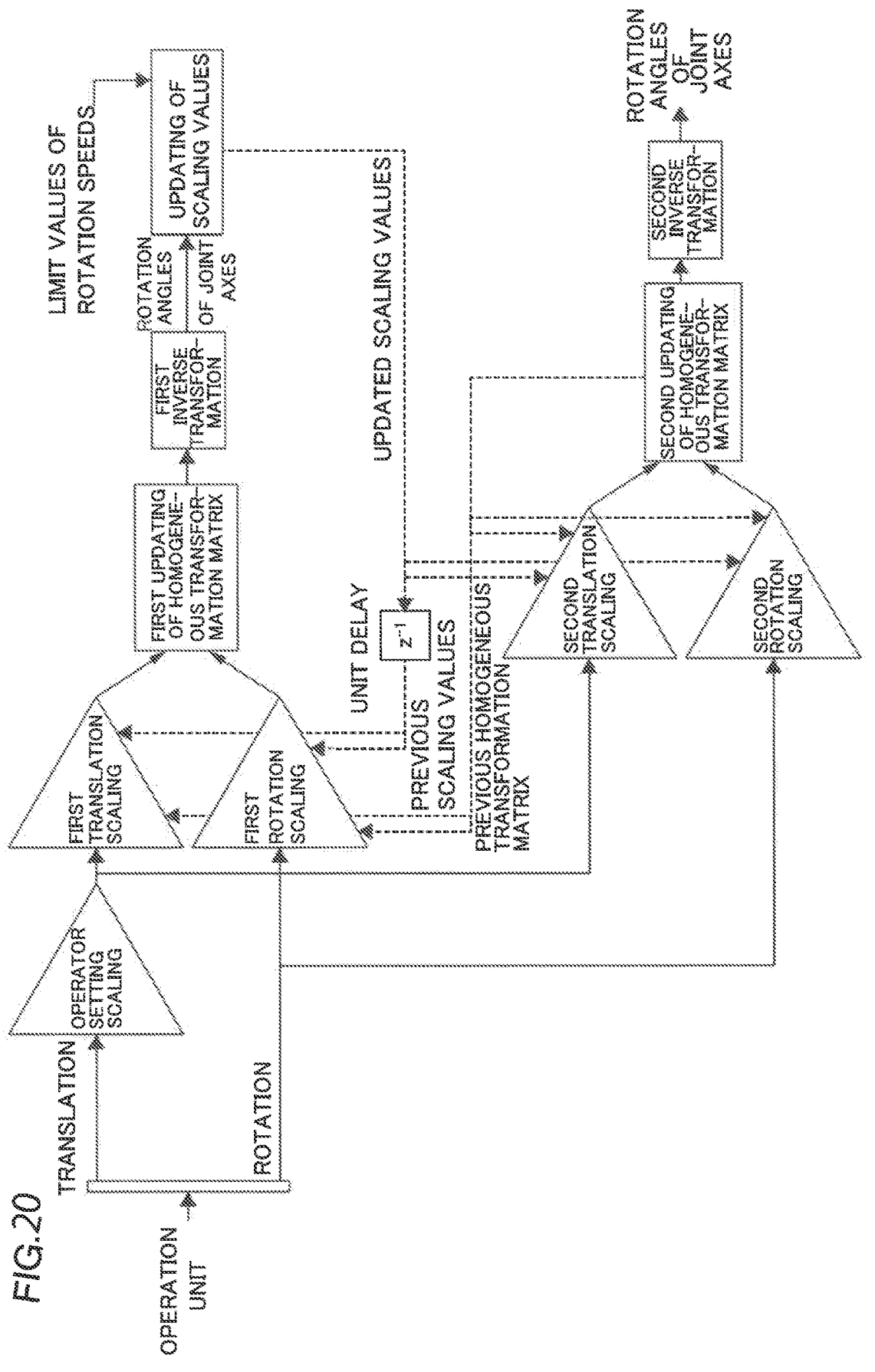
FIG. 20 is a diagram for illustrating operator setting scaling, translation scaling, and rotation scaling according to the first embodiment.

As shown in FIG. 20, the operation of the operator is received by the operation unit 120. Thus, a homogeneous transformation matrix corresponding to the received operation is produced. The homogeneous transformation matrix is a 4×4 matrix. The homogeneous transformation matrix includes a translational component for translation of the surgical instrument 4 and a rotational component for rotation of the surgical instrument 4. The control device 130 calculates a difference between the current position of the surgical instrument 4 and a target position received by the operation unit 120. The position corresponds to the translational component of the homogeneous transformation matrix. The control device 130 calculates a difference between the current posture of the surgical instrument 4 and a target posture received by the operation unit 120. The posture corresponds to the rotational component of the homogeneous transformation matrix. The control device 130 calculates a target homogeneous transformation matrix based on the calculated difference values. That is, the homogeneous transformation matrix is updated. The control device 130 performs an inverse kinematics calculation on the updated homogeneous transformation matrix. The control device 130 calculates the rotation angles of joint axes with respect to the robot arm 60 and the surgical instrument 4 by the inverse kinematics calculation. Thus, the control device 130 controls the translation and rotation of the surgical instrument 4 based on the received operation amount.

In the first embodiment, the remote control apparatus 2 receives an operator setting scaling value for translation of the surgical instrument 4 by the operator. For example, the operator setting scaling value is received by the touch panel 23 of the remote control apparatus 2. The control device 130 performs operator setting scaling on the translational component of the operation received by the operation unit 120. The operator setting scaling indicates that the surgical instrument 4 is moved by an amount obtained by multiplying the operation amount of the operation unit 120 operated by the operator by a ratio corresponding to the operator setting scaling value. For example, when the operator setting scaling value is set to 3:1 and the operation amount by the operator is 3, the surgical instrument 4 is translated by 1. The operator setting scaling is not performed on the rotational component. The touch panel 23 is an example of a receiver. The operator setting scaling is an example of second scaling.

The remote control apparatus 2 receives operator setting scaling values for the robot arms 60a, 60b, and 60d to which the surgical instruments 4 other than the endoscope 6 are attached. In the first embodiment, when the remote control apparatus 2 receives an operator setting scaling value for any one of the robot arms 60a, 60b, and 60d, the control device 130 sets an operator setting scaling value for the robot arm 60c to which the endoscope 6 is attached in conjunction with the received operator setting scaling value. For example, when an operator setting scaling value of 3:1 is received for any one of the robot arms 60a, 60b, and 60d, an operator setting scaling value of 3:1 is automatically set for the robot arm 60c. The operator setting scaling values set for the robot arms 60a, 60b, and 60d to which the surgical instruments 4 other than the endoscope 6 are attached are examples of a second scaling value. The operator setting scaling value set for the robot arm 60c to which the endoscope 6 is attached is an example of a third scaling value.

In the first embodiment, when the remote control apparatus 2 receives an operation to increase the operator setting scaling value for any one of the robot arms 60a, 60b, and 60d, the control device 130 increases the operator setting scaling value for the robot arm 60c. For example, when a change is received to increase the operator setting scaling value from 3:1 to 2:1 for any one of the robot arms 60a, 60b, and 60d, the operator setting scaling value for the robot arm 60c is automatically set to increase from 3:1 to 2.3:1. When a change is received to increase the operator setting scaling value from 2:1 to 1.5:1 for any one of the robot arms 60a, 60b, and 60d, the operator setting scaling value for the robot arm 60c is automatically set to increase from 2.3:1 to 2:1.

In the first embodiment, the control device 130 performs rotation scaling on at least the rotational component of the translational component of the surgical instrument 4 and the rotational component of the surgical instrument 4 in the received operation amount. Specifically, in the first embodiment, the control device 130 performs the translation scaling on the translational component and rotation scaling on the rotational component. For translation of the surgical instrument 4, the control device 130 performs the translation scaling on the translational component on which the operator setting scaling has been performed. For rotation of the surgical instrument 4, the control device 130 performs only the rotation scaling. The translation scaling and the rotation scaling are examples of first scaling.

In the first embodiment, the control device 130 performs the translation scaling and the rotation scaling such that the rotation speeds of the joint axes of the robot arm 60 and the surgical instrument 4 are equal to or lower than a limit value. The control device 130 does not perform the translation scaling or rotation scaling when the rotation speeds of the joint axes of the robot arm 60 and the surgical instrument 4 are lower than the limit value. The control device 130 performs only the operator setting scaling described below. The translation scaling and the rotation scaling are described below in detail. The joint axes of the surgical instrument 4 refer to a plurality of joint axes of the surgical instrument 4 including the roll rotation axis of the shaft 4c and the JT10 axis, which is the rotation axis of the wrist joint.

In the first embodiment, the control device 130 performs the first translation scaling on the translational component using the translation scaling value used in a previous control cycle. Furthermore, the control device 130 performs the first rotation scaling on the rotational component using the rotation scaling value used in the previous control cycle. Thus, the first updating of the homogeneous transformation matrix is performed. Then, the control device 130 calculates the rotation angles of the joint axes of the robot arm 60 and the surgical instrument 4 by performing the first inverse kinematics calculation on the translational component on which the translation scaling has been performed and the rotational component on which the rotation scaling has been performed. The control device 130 updates the translation scaling value and the rotation scaling value such that the rotation speeds of the joint axes of the robot arm 60 become equal to or lower than the limit value. The control device 130 performs the second translation scaling using the updated translation scaling value and the second rotation scaling using the updated rotation scaling value. Thus, the second updating of the homogeneous transformation matrix is performed. After that, the control device 130 calculates the rotation angles of the joint axes of the robot arm 60 and the surgical instrument 4 by performing the second inverse kinematics calculation on the translational component and the rotational component. The translation scaling value and the rotation scaling value are automatically adjusted by the control device 130, and thus they cannot be adjusted by the operation of the operator. A unit delay in FIG. 20 indicates using the translation and rotation scaling values used in the previous control cycle. The initial values of the translation scaling value and the rotation scaling value are 1. However, the initial values are not limited to this as long as the same are a positive value. The translation scaling value and the rotation scaling value are examples of a first scaling value.

Translation Scaling

Figure 21:
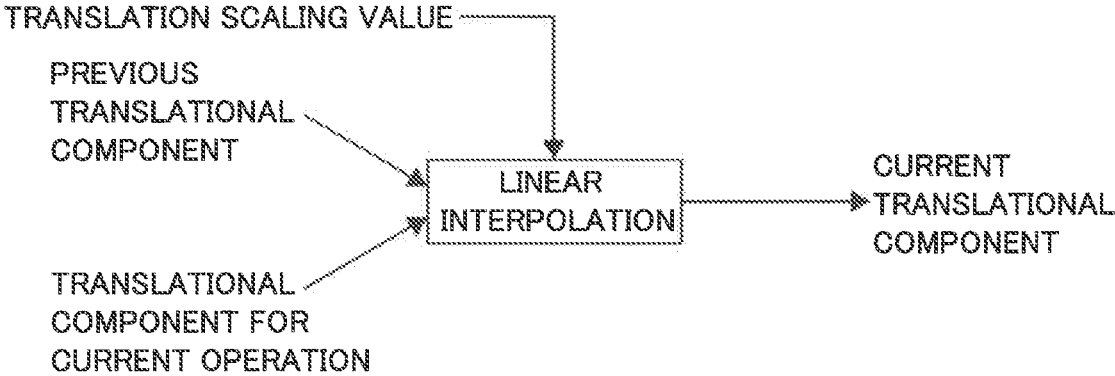
FIG. 21 is a diagram for illustrating linear interpolation of a translation scaling value according to the first embodiment.

As shown in FIG. 21, the control device 130 calculates the translational component used in a current control cycle by linearly interpolating the translational component used in the previous control cycle and the translational component corresponding to the operation amount received by the operation unit 120 based on the translation scaling value. Thus, the translation scaling is performed. In the first translation scaling, the translation scaling value used in the previous control cycle is used. In the second translation scaling, the translation scaling value updated such that the rotation speeds of the joint axes of the robot arm 60 become equal to or lower than the limit value is used.

Even when the translation scaling is performed, the movement direction of the surgical instrument 4 does not change, but the movement amount of the surgical instrument 4 becomes smaller than the operation amount of the operation unit 120 operated by the operator. On the other hand, the operator setting scaling is also performed on the translational component of the surgical instrument 4, and thus even when the movement amount of the surgical instrument 4 is reduced by the translation scaling, the operator feels little discomfort.

Rotation Scaling

Figure 22:
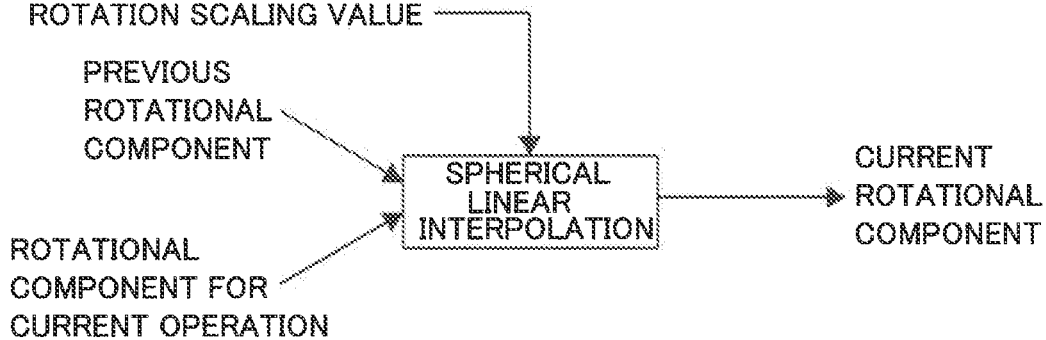
FIG. 22 is a diagram for illustrating spherical linear interpolation of a rotation scaling value according to the first embodiment.

As shown in FIG. 22, the control device 130 calculates the rotational component used in the current control cycle by performing a spherical linear interpolation to interpolate the rotational component used in the previous control cycle and the rotational component corresponding to the operation amount received by the operation unit 120 along the spherical surface based on the rotation scaling value. Thus, the rotation scaling is performed. In the first rotation scaling, the rotation scaling value used in the previous control cycle is used. In the second rotation scaling, the rotation scaling value updated such that the rotation speeds of the joint axes of the robot arm 60 become equal to or lower than the limit value is used.

Even when the rotation speeds of the joint axes of the robot arm 60 are limited to the limit value or lower by the rotation scaling, the surgical instrument 4 does not rotate according to an operation received by the operation unit 120 immediately after the limitation of the rotation speeds. Immediately after the limitation of the rotation speeds, the surgical instrument 4 gradually rotates to catch up with the received operation. The surgical instrument 4 eventually rotates to correspond to the received operation. It is important that the surgical instrument 4 is in a posture intended by the operator, and thus it is important that the surgical instrument 4 is eventually in a posture corresponding to the received operation. The posture refers to a direction in which the pair of forceps 4*b* or the pair of scissors as the surgical instrument 4 is directed.

Updating of Translation Scaling Value and Rotation Scaling Value

Figure 23:
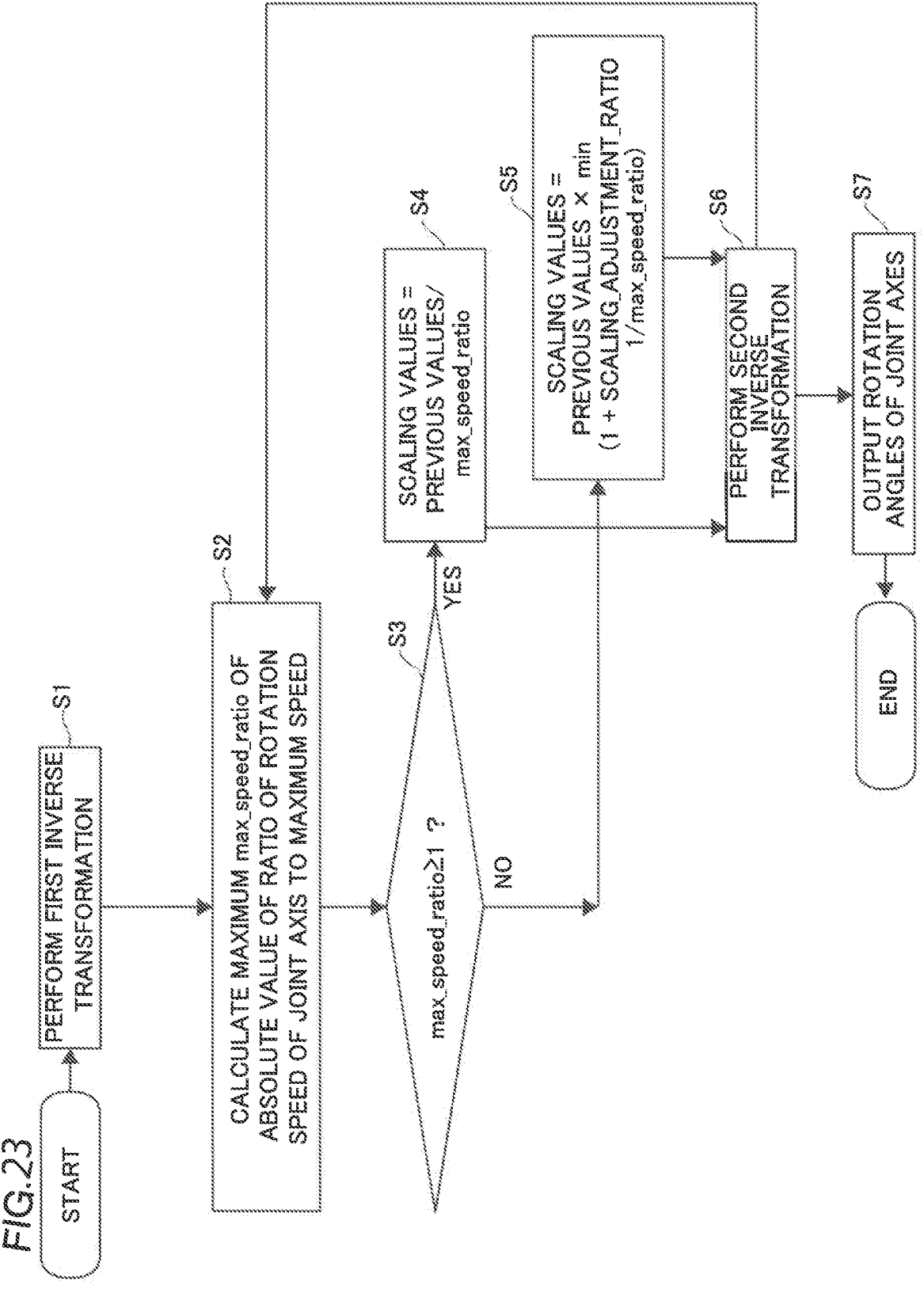
FIG. 23 is a flowchart for illustrating updating of the translation and rotation scaling values according to the first embodiment.

Updating of the translation scaling value and the rotation scaling value is now described with reference to FIG. 23. In step S1, the control device 130 performs the first translation scaling on the translational component using the previous translation scaling value, and performs the first rotation scaling on the rotational component using the rotation scaling value used in the previous control cycle. Then, the control device 130 performs the first inverse kinematics calculation on the homogeneous transformation matrix on which the first translation scaling and the first rotation scaling have been performed to calculate the rotation angles of the joint axes of the robot arm 60 and the surgical instrument 4.

In the first embodiment, in step S2, the control device 130 calculates the rotation angles of the plurality of joint axes of the robot arm 60 and the surgical instrument 4. The control device 130 calculates the rotation speed of each of the plurality of joint axes based on the rotation angle of each of the plurality of joint axes. The control device 130 calculates the absolute value of the ratio of the calculated rotation speed to the limit value of each axis for each axis. The control device 130 sets the largest value among the calculated absolute values of the ratios for the respective axes to max_speed_ratio.

In step S3, the control device 130 determines whether or not the maximum rotation speed among the rotation speeds of the plurality of joint axes is equal to or higher than the limit value. Specifically, the control device 130 determines whether or not max_speed_ratio is 1 or more.

When YES in step S3, the control device 130 advances to step S4. That is, when the maximum rotation speed among the rotation speeds of the plurality of joint axes is equal to or higher than the limit value, the control device 130 changes the translation scaling value and the rotation scaling value such that the translation scaling value and the rotation scaling value become smaller in step S4. Specifically, in the first embodiment, the control device 130 sets a value obtained by dividing the translation scaling value used in the previous control cycle by a value based on the maximum rotation speed as a post-change translation scaling value. The control device 130 sets a value obtained by dividing the rotation scaling value used in the previous control cycle by the value based on the maximum rotation speed as a post-change rotation scaling value. More specifically, the control device 130 sets the value obtained by dividing the previous translation scaling value by max_speed_ratio as an updated translation scaling value. The control device 130 sets the value obtained by dividing the previous rotation scaling value by max_speed_ratio as an updated rotation scaling value. Then, the control device 130 advances to step S6.

When NO in step S3, the control device 130 advances to step S5. That is, when the maximum rotation speed among the rotation speeds of the plurality of joint axes is lower than the limit value, the control device 130 changes the translation scaling value and the rotation scaling value such that the translation scaling value and the rotation scaling value become larger. Specifically, in the first embodiment, the control device 130 sets, as a post-change translation scaling value, a value obtained by multiplying the smaller of the value obtained by dividing the translation scaling value used in the previous control cycle by the value based on the maximum rotation speed and a predetermined value greater than a preset value of 1 by the translation scaling value used in the previous control cycle. The control device 130 sets, as a post-change rotation scaling value, a value obtained by multiplying the smaller of the value obtained by dividing the rotation scaling value used in the previous control cycle by the value based on the maximum rotation speed and the predetermined value greater than a preset value of 1 by the rotation scaling value used in the previous control cycle. More specifically, the control device 130 sets, as the post-change translation scaling value, the value obtained by multiplying the smaller of the value obtained by dividing the translation scaling value used in the previous control cycle by max_speed_ratio and 1+SCALING_ADJUSTMENT_RATIO by the translation scaling value used in the previous control cycle. The control device 130 sets, as the post-change rotation scaling value, the value obtained by multiplying the smaller of the value obtained by dividing the rotation scaling value used in the previous control cycle by max_speed_ratio and 1+SCALING_ADJUSTMENT_RATIO by the rotation scaling value used in the previous control cycle. SCALING_ADJUSTMENT_RATIO is 0.03, for example.

Then, in step S6, the control device 130 performs the second translation scaling based on the updated translation scaling value, and performs the second rotation scaling based on the updated rotation scaling value. Then, the control device 130 performs the second inverse kinematics calculation on the translational component on which the second translation scaling has been performed and the rotational component on which the second rotation scaling has been performed.

Then, in step S7, the control device 130 calculates the rotation angles of the joint axes of the robot arm 60 and the surgical instrument 4. The translation scaling and the rotation scaling are performed using the same algorithm shown in step S1 to step S7 described above.

Joint Axes Subject to Translation Scaling and Rotation Scaling

In the first embodiment, for the robot arms 60a, 60b, and 60d having tip ends to which the surgical instruments 4 other than the endoscope 6 are attached, the control device 130 performs the translation scaling and the rotation scaling on a plurality of joint axes other than the joint axes involved in opening and closing the jaw member 104a and the jaw member 104b of the surgical instrument 4. The joint axes involved in opening and closing the jaw member 104a and the jaw member 104b are the JT11 axis and the JT12 axis. The plurality of joint axes other than the joint axes involved in opening and closing the jaw member 104a and the jaw member 104b are the JT1 to JT10 axes.

Figure 24:
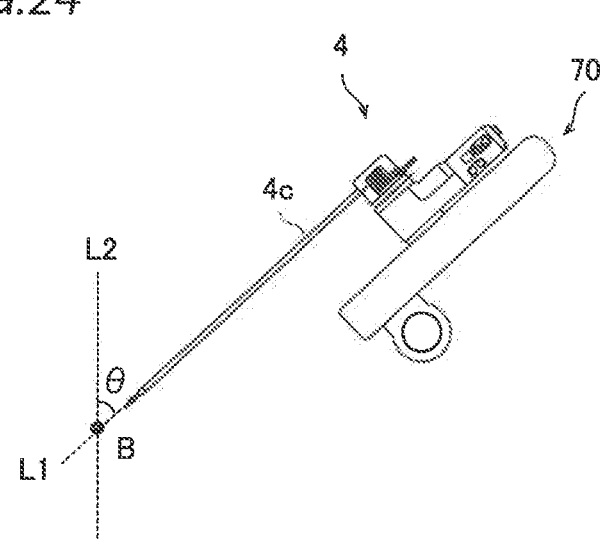
FIG. 24 is a diagram for illustrating a virtual axis according to the first embodiment.

In the first embodiment, as shown in FIG. 24, for the robot arms 60a, 60b, and 60d having tip ends to which the surgical instruments 4 other than the endoscope 6 are attached, the control device 130 performs the translation scaling and the rotation scaling on a virtual axis B on which the surgical instrument 4 rotates about a predetermined point in addition to the plurality of joint axes other than the joint axes involved in opening and closing the jaw member 104a and the jaw member 104b of the surgical instrument 4. The predetermined point refers to a point at which a straight line L1 along the direction in which the shaft 4c extends and a straight line L2 along the vertical direction intersect with each other. That is, the control device 130 performs the translation scaling and the rotation scaling such that the rotation speeds of the joint axes of the robot arm 60 and the surgical instrument 4 become equal to or lower than the limit value when the surgical instrument 4 moves to rotate about the axis B. In other words, the translation scaling and the rotation scaling are performed such that the angular velocity of an angle θ defined by the straight line L1 and the straight line L2 is equal to or less than a limit value.

For the robot arm 60c having a tip end to which the endoscope 6 is attached, the control device 130 performs the translation scaling and the rotation scaling on the JT1 to JT9 axes and the virtual axis B.

The operator can move the robot arm 60 and the surgical instrument 4 such that the robot arm 60 and the surgical instrument 4 approach singular postures thereof by operating the arm operation unit 80 attached to the robot arm 60. The singular postures refer to postures in which the robot arm 60 and the surgical instrument 4 cannot be controlled. For example, the postures in which the robot arm 60 and the surgical instrument 4 are fully extended are singular postures. As the robot arm 60 and the surgical instrument 4 approach the singular postures, the rotation speeds of the joint axes rapidly increase, but the translation scaling and the rotation scaling can significantly reduce or prevent a rapid increase in the rotation speeds of the joint axes.

A control method of the robotic surgical system 100 is now described with reference to FIG. 25.

In step S11, an operation is received by the operation unit 120.

In step S12, the control device 130 performs the operator setting scaling on the translational component of the homogeneous transformation matrix corresponding to the operation amount of the received operation. The operator setting scaling value is received in advance by the touch panel 23 of the remote control apparatus 2.

In step S13, the control device 130 performs the first translation scaling using the previous translation scaling value and the first rotation scaling using the previous rotation scaling value on the translational and rotational components of the homogeneous transformation matrix on which the operator setting scaling has been performed, respectively.

In step S14, the control device 130 performs the first inverse kinematics calculation on the homogeneous transformation matrix on which the first translation scaling and the first rotation scaling have been performed to calculate the rotation angles of the joint axes of the robot arm 60 and the surgical instrument 4.

In step S15, the control device 130 updates the translation scaling value and the rotation scaling value such that the rotation speeds of the joint axes of the robot arm 60 and the surgical instrument 4 become equal to or lower than the limit value.

In step S16, the control device 130 performs the second translation scaling using the updated translation scaling value and the second rotation scaling using the updated rotation scaling value on the translational and rotational components of the homogeneous transformation matrix, respectively.

In step S17, the control device 130 performs the second inverse kinematics calculation on the homogeneous transformation matrix on which the second translation scaling and the second rotation scaling have been performed to calculate the rotation angles of the joint axes of the robot arm 60 and the surgical instrument 4. The operations in step S11 to step S17 are repeated every control cycle.

Advantages of First Embodiment

According to the first embodiment, the following advantages are achieved.

According to the first embodiment, as described above, the control device 130 is configured or programmed to perform the translation scaling on the translational component of the surgical instrument 4 in the received operation amount and perform the rotation scaling on the rotational component of the surgical instrument 4 in the received operation amount. The rotational component greatly contributes to the posture of the robot arm 60, and thus the rotation scaling is performed on at least the rotational component such that the rotation scaling can be effectively performed on the posture of the robot arm 60.

According to the first embodiment, as described above, the control device 130 is configured or programmed to perform the translation scaling and the rotation scaling such that the rotation speeds of the joint axes of the robot arm 60 and the surgical instrument 4 become equal to or lower than the limit value. Accordingly, driving of the joint axes of the robot arm 60 beyond the rotation speeds can be significantly reduced or prevented.

According to the first embodiment, as described above, the control device 130 is configured or programmed to perform the translation scaling and the rotation scaling using the translation and rotation scaling values used in the previous control cycle, perform the inverse kinematics calculation on the translational component and the rotational component on which the translation scaling and the rotation scaling have been performed to calculate the rotation angles of the joint axes of the robot arm 60 and the surgical instrument 4, update the translation and rotation scaling values such that the rotation speeds of the joint axes of the robot arm 60 and the surgical instrument 4 become equal to or lower than the limit value, and perform the inverse kinematics calculation on the translational component and the rotational component on which the translation scaling and the rotation scaling have been performed using the updated translation and rotation scaling values to calculate the rotation angles of the joint axes of the robot arm 60 and the surgical instrument 4. When the rotation angles are corrected such that the rotation speeds become equal to or lower than the limit value after the rotation angles of the joint axes of the robot arm 60 and the surgical instrument 4 are calculated, the locus of movement of the surgical instrument 4 may deviate from a locus intended by the operator. For example, when the surgical instrument 4 is being translated, the direction of the translation may be skewed due to the limitation of the rotation speeds. Furthermore, in the robotic surgical system, the robot arm 60 is driven such that the surgical instrument 4 rotates with the preset pivot position PP as a fulcrum. However, the surgical instrument 4 may rotate with a position deviated from the pivot position PP as a fulcrum due to the limitation of the rotation speeds. Therefore, the inverse kinematics calculation is performed on the translational component and the rotational component on which the translation scaling and the rotation scaling have been performed such that a deviation of the locus of movement of the surgical instrument 4 from the locus intended by the operator can be significantly reduced or prevented.

According to the first embodiment, as described above, the control device 130 is configured or programmed to calculate the rotation angles of the plurality of joint axes, calculate the rotation speeds of the plurality of joint axes based on the rotation angles of the plurality of joint axes, and change the translation and rotation scaling values such that the translation and rotation scaling values become smaller when the maximum rotation speed among the rotation speeds of the plurality of joint axes is equal to or higher than the limit value. Accordingly, the translation and rotation scaling values are changed based on the maximum rotation speed, and thus even when there are a plurality of joint axes of which the rotation speeds become equal to or higher than the limit value, the rotation speeds of all the joint axes of which the rotation speeds become equal to or higher than the limit value can be lower than the limit value.

According to the first embodiment, as described above, the control device 130 is configured or programmed to set the values obtained by dividing the translation and rotation scaling values used in the previous control cycle by the value based on the maximum rotation speed as the post-change translation and rotation scaling values. Accordingly, the post-change translation and rotation scaling values are relatively small, and thus the rotation speeds can be quickly prevented from becoming equal to or higher than the limit value.

According to the first embodiment, as described above, the control device 130 is configured or programmed to change the translation and rotation scaling values such that the translation and rotation scaling values become larger when the maximum rotation speed among the rotation speeds of the plurality of joint axes is lower than the limit value. Accordingly, when the rotation speeds do not exceed the limit value, the translation scaling and the rotation scaling are performed such that the operation of the medical manipulator 1 approaches the received operation amount. Therefore, the movement amount of the surgical instrument 4 can be close to the amount of operation by the operator.

According to the first embodiment, as described above, the control device 130 is configured or programmed to set, as the post-change translation and rotation scaling values, the values obtained by multiplying the smaller of the values obtained by dividing the translation and rotation scaling values used in the previous control cycle by the value based on the maximum rotation speed and the predetermined value greater than a preset value of 1 by the translation and rotation scaling values used in the previous control cycle. Accordingly, differences between the pre-change translation and rotation scaling values and the post-change translation and rotation scaling values are relatively small, and thus the movement amount of the surgical instrument 4 can be smoothly close to the amount of operation by the operator.

According to the first embodiment, as described above, the control device 130 is configured or programmed to calculate the translational component used in the current control cycle by linearly interpolating the translational component used in the previous control cycle and the translational component corresponding to the operation amount received by the operation unit 120 based on the post-change translation scaling value. Accordingly, the translational component used in the current control cycle is calculated by relatively simple linear interpolation, and thus the control load on the control device 130 can be reduced.

According to the first embodiment, as described above, the control device 130 is configured or programmed to calculate the rotational component used in the current control cycle by performing the spherical linear interpolation to interpolate the rotational component used in the previous control cycle and the rotational component corresponding to the operation amount received by the operation unit 120 along the spherical surface based on the post-change rotation scaling value. Accordingly, the rotational component used in the current control cycle is calculated by relatively simple spherical linear interpolation, and thus the control load on the control device 130 can be reduced.

According to the first embodiment, as described above, the control device 130 is configured or programmed to perform the translation scaling and the rotation scaling on both the translational component and the rotational component, respectively. In the robotic surgical system 100, when a distance between the pivot position PP and the tip end of the surgical instrument 4 is small, the robot arm 60 is moved by a relatively large amount in order to move the tip end of the surgical instrument 4 by a desired distance. In such a case, the rotation speeds of the joint axes of the robot arm 60 become relatively high, and thus performing the translation scaling and the rotation scaling on both the translational component and the rotational component, respectively, is particularly effective in significantly reducing or preventing an excessive increase in the rotation speeds of the joint axes of the robot arm 60.

According to the first embodiment, as described above, the control device 130 is configured or programmed to perform the operator setting scaling on the translational component based on the received operator setting scaling value, and perform the translation scaling on the translational component on which the operator setting scaling has been performed. Accordingly, the operator setting scaling value is changed such that the amount of translation of the surgical instrument 4 can be adjusted according to the preference of the operator.

According to the first embodiment, as described above, the control device 130 is configured or programmed to set the operator setting scaling value for the robot arm 60c in conjunction with the received operator setting scaling value when the touch panel 23 receives the operator setting scaling values for the robot arms 60a, 60b, and 60d. Accordingly, the operator setting scaling values for the robot arm 60c and each of the robot arms 60a, 60b, and 60d are set in conjunction with each other. Therefore, a difference between the operation feeling of the operator with respect to the robot arm 60c and the operation feeling of the operator with respect to the robot arms 60a, 60b, and 60d can be significantly reduced or prevented.

According to the first embodiment, as described above, the control device 130 is configured or programmed to increase the operator setting scaling values for the robot arms 60a, 60b, and 60d when the touch panel 23 receives an operation to increase the operator setting scaling values for the robot arms 60a, 60b, and 60d. Accordingly, the operator setting scaling values for the robot arm 60c and each of the robot arms 60a, 60b, and 60d are changed in conjunction with each other in the same direction. Therefore, a difference between the operation feeling of the operator with respect to the robot arm 60c and the operation feeling of the operator with respect to the robot arms 60a, 60b, and 60d can be effectively significantly reduced or prevented.

According to the first embodiment, as described above, the control device 130 is configured or programmed to perform the translation scaling and the rotation scaling on the plurality of joint axes other than the joint axes involved in opening and closing the jaw member 104a and the jaw member 104b of the surgical instrument 4. When the translation scaling and the rotation scaling are performed due to the opening and closing of the jaw member 104a and the jaw member 104b, the translation scaling and the rotation scaling may be performed unnecessarily with respect to the operation of the robot arm 60. Therefore, in the first embodiment, the translation scaling and the rotation scaling are performed on the plurality of joint axes other than the joint axes involved in opening and closing the jaw member 104a and the jaw member 104b of the surgical instrument 4 such that unnecessary translation scaling and rotation scaling with respect to the operation of the robot arm 60 can be significantly reduced or prevented.

According to the first embodiment, as described above, the control device 130 is configured or programmed to perform the translation scaling and the rotation scaling on the virtual axis B on which the surgical instrument 4 rotates about the predetermined point. Accordingly, excessively high-speed movement of the entire robot arm 60 with respect to the virtual axis B can be significantly reduced or prevented.

According to the first embodiment, as described above, the predetermined point is a point at which the straight line L1 along the direction in which the shaft 4c extends and the straight line L2 along the vertical direction intersect with each other. Accordingly, excessively high-speed movement of the robot arm 60 and the surgical instrument 4 about the point at which the straight line L1 along the direction in which the shaft 4c extends and the straight line L2 along the vertical direction intersect with each other can be significantly reduced or prevented.

Second Embodiment

Updating of a translation scaling value and a rotation scaling value according to a second embodiment is now described with reference to FIG. 26.

As shown in FIG. 26, in step S21, a control device 130 performs the first translation scaling on a translational component using a translation scaling value used in a previous control cycle, and performs the first rotation scaling on a rotational component using a rotation scaling value used in the previous control cycle. Then, the control device 130 performs the first inverse kinematics calculation on a homogeneous transformation matrix on which the first translation scaling and the first rotation scaling have been performed to calculate the rotation angles of joint axes of a robot arm 60 and a surgical instrument 4.

In step S22, the control device 130 calculates the rotation angles of a plurality of joint axes of the robot arm 60 and the surgical instrument 4. The control device 130 calculates the rotation speed of each of the plurality of joint axes based on the rotation angle of each of the plurality of joint axes. The control device 130 calculates the absolute value of the ratio of the calculated rotation speed to the limit value of each axis for each axis. The control device 130 sets the largest value among the calculated absolute values of the ratios for the respective axes to max_speed_ratio.

In step S23, the control device 130 determines whether or not the maximum rotation speed among the rotation speeds of the plurality of joint axes is higher than the limit value. Specifically, the control device 130 determines whether or not max_speed_ratio is greater than 1.

When YES in step S23, the control device 130 advances to step S24. The control device 130 sets a value obtained by multiplying the translation scaling value used in the previous control cycle by 1−SCALING_ADJUSTMENT_RATIO as a post-change translation scaling value. The control device 130 sets a value obtained by multiplying the rotation scaling value used in the previous control cycle by 1−SCALING_ADJUSTMENT_RATIO as a post-change rotation scaling value. Then, the control device 130 advances to step S25.

In step S25, the control device 130 performs the second inverse kinematics calculation on the homogeneous transformation matrix on which the translation scaling has been performed using the post-change translation scaling value, and the rotation scaling has been performed using the post-change rotation scaling value. Then, the control device 130 returns to step S22.

When NO in step S23, the control device 130 advances to step S27. In step S27, the control device 130 determines whether or not max_speed_ratio is less than 1. When YES in step S27, the control device 130 advances to step S26, and outputs the rotation angles of the joint axes of the robot arm 60 and the surgical instrument 4.

When YES in step S27, the control device 130 advances to step S28, and sets a value obtained by multiplying the translation scaling value used in the previous control cycle by 1+SCALING_ADJUSTMENT_RATIO as the post-change translation scaling value. Furthermore, the control device 130 sets a value obtained by multiplying the rotation scaling value used in the previous control cycle by 1+SCALING_ADJUSTMENT_RATIO as the post-change rotation scaling value.

In step S29, when the post-change translation scaling value is greater than a first reference value, the control device 130 sets the post-change translation scaling value as the first reference value. When the post-change rotation scaling value is greater than a second reference value, the control device 130 sets the post-change rotation scaling value as the second reference value. The first reference value is a predetermined scaling reference value. The second reference value is 1. Then, after advancing to step S25, the control device 130 returns to step S22.

After repeating the loop of step S22, step S23, step S24, and step S25, or the loop of step S22, step S23, step S27, step S28, step S29, and step S25 SCALING_ADJUST-MENT_LOOPMAX times, the control device 130 advances to step S26, and outputs the rotation angles of the joint axes of the robot arm 60 and the surgical instrument 4. SCAL-ING_ADJUSTMENT_LOOPMAX refers to the number of calculations repeated in one control cycle of the control device 130. SCALING_ADJUSTMENT_LOOPMAX is five times, for example. The above loop calculation is repeated such that the rotation speeds of the joint axes approach the limit value within a range not exceeding the limit value. Furthermore, the translation scaling and the rotation scaling are performed using the same algorithm shown in step S21 to step S29 described above.

MODIFIED EXAMPLES

The embodiments disclosed this time must be considered as illustrative in all points and not restrictive. The scope of the present disclosure is not shown by the above description of the embodiments but by the scope of claims for patent, and all modifications or modified examples within the meaning and scope equivalent to the scope of claims for patent are further included.

For example, while calculations such as translation scaling, rotation scaling, and an inverse kinematics calculation are performed by the control device 130 that controls the entire robotic surgical system 100 in each of the aforementioned first and second embodiments, the present disclosure is not limited to this. Calculations such as translation scaling, rotation scaling, and an inverse kinematics calculation may alternatively be performed by a control device other than the control device 130 that controls the entire robotic surgical system 100.

While the control device 130 is arranged inside the medical manipulator 1 in each of the aforementioned first and second embodiments, the present disclosure is not limited to this. For example, the control device 130 may alternatively be arranged outside the medical manipulator 1.

While the control device 130 performs both the translation scaling and the rotation scaling in each of the aforementioned first and second embodiments, the present disclosure is not limited to this. For example, the control device 130 may alternatively perform only the rotation scaling.

While the translation scaling and the rotation scaling are performed on the plurality of joint axes of the robot arm 60 and the surgical instrument 4 in each of the aforementioned first and second embodiments, the present disclosure is not limited to this. For example, the translation scaling and the rotation scaling may alternatively be performed on only one of the plurality of joint axes of the robot arm 60 and the surgical instrument 4.

While the translational component used in the previous control cycle and the translational component corresponding to the operation amount received by the operation unit 120 are linearly interpolated in each of the aforementioned first and second embodiments, the present disclosure is not limited to this. The translational component used in the previous control cycle and the translational component corresponding to the operation amount received by the operation unit 120 may alternatively be interpolated by a method other than linear interpolation.

While spherical linear interpolation is performed on the rotational component used in the previous control cycle and the rotational component corresponding to the operation amount received by the operation unit 120 in each of the aforementioned first and second embodiments, the present disclosure is not limited to this. For example, element interpolation of Euler angles may alternatively be performed on the rotational component used in the previous control cycle and the rotational component corresponding to the operation amount received by the operation unit 120. The Euler angles refer to rotation angles RX, RY, and RZ around an X-axis, a Y-axis, and a Z-axis. The element interpolation of Euler angles refers to spline interpolation of rotations around axes in the previous control cycle and the current control cycle. For example, for the robot arm 60c having a tip end to which the endoscope 6 is attached, the rotation angles of the joints may be calculated using variables RX, RY, RZ, and Z. The control device 130 interpolates the variables of RX, RY, RZ, and Z in the previous control cycle and the current control cycle for the robot arm 60c. Thus, the control device 130 calculates the rotation angles of joint axes of the robot arm 60c.

While the operator setting scaling values for the robot arms 60a, 60b, and 60d having tip ends to which the surgical instruments 4 other than the endoscope 6 are attached and the robot arm 60c having a tip end to which the endoscope 6 is attached are changed in conjunction with each other in each of the aforementioned first and second embodiments, the present disclosure is not limited to this. For example, the operator setting scaling values for the robot arms 60a, 60b, and 60d having tip ends to which the surgical instruments 4 other than the endoscope 6 are attached, and the operator setting scaling value for the robot arm 60c having a tip end to which the endoscope 6 is attached may alternatively be set individually.

While four robot arms 60 are provided in each of the aforementioned first and second embodiments, the present disclosure is not limited to this. In the present disclosure, the number of robot arms 60 may be any number as long as at least one robot arm is provided.

While each of the arm portion 61 and the positioner 40 includes a 7-axis articulated robot in each of the aforementioned first and second embodiments, the present disclosure is not limited to this. For example, each of the arm portion 61 and the positioner 40 may alternatively include an articulated robot having an axis configuration other than the 7-axis articulated robot. The axis configuration other than the 7-axis articulated robot refers to six axes or eight axes, for example.

While the medical manipulator 1 includes the medical cart 3, the positioner 40, and the arm base 50 in each of the aforementioned first and second embodiments, the present disclosure is not limited to this. For example, the medical manipulator 1 may not include the medical cart 3, the positioner 40, or the arm base 50, but may include only the robot arms 60.

While the translation scaling and the rotation scaling are performed on the joint axes of the robot arm 60 and the surgical instrument 4 in each of the aforementioned first and second embodiments, the present disclosure is not limited to this. For example, the translation scaling and the rotation scaling may alternatively be performed on only the joint axes of the robot arm 60.

The functionality of the elements disclosed herein may be implemented using circuitry or processing circuitry that includes general purpose processors, special purpose processors, integrated circuits, application specific integrated circuits (ASICs), conventional circuitry and/or combinations thereof that are configured or programmed to perform the disclosed functionality. Processors are considered processing circuitry or circuitry as they include transistors and other circuitry therein. In the present disclosure, the circuitry, units, or means are hardware that carries out or is programmed to perform the recited functionality. The hardware may be hardware disclosed herein or other known hardware that is programmed or configured to carry out the recited functionality. When the hardware is a processor that may be considered a type of circuitry, the circuitry, means, or units are a combination of hardware and software, and the software is used to configure the hardware and/or processor.

What is claimed is:

1. A robotic surgical system comprising:
a patient-side apparatus including a robot arm having a tip end to which a surgical instrument is attached;
an operator-side apparatus including an operation unit to receive an operation amount for the surgical instrument; and
a control device configured or programmed to perform operations comprising operations to control translation and rotation of the surgical instrument based on the received operation amount; wherein
the control device is configured or programmed to perform operations comprising operations to:
perform first scaling on a translational component and a rotational component of the surgical instrument in the received operation amount;
calculate a rotation angle of a joint axis of the robot arm by performing an inverse kinematics calculation on the translational component and the rotational component after the first scaling is performed;
perform the first scaling with a first scaling value such that a rotation speed of the joint axis of the robot arm becomes equal to or lower than a limit value;
control translation and rotation of the surgical instrument based on the received operation amount and the first scaling value;
calculate rotation angles of a plurality of joint axes of the robot arm;
calculate rotation speeds of the plurality of joint axes based on the rotation angles of the plurality of joint axes;
change the first scaling value such that the first scaling value becomes larger when a maximum rotation speed among the calculated rotation speeds of the plurality of joint axes of the robot arm is lower than the limit value; and
control translation and rotation of the surgical instrument based on the received operation amount and the changed first scaling value, and the calculation of the rotation angle of the joint axis is performed by the inverse kinematics calculation using a homogenous transformation matrix including the translational component and the rotational component after the first scaling is performed.

2. The robotic surgical system according to claim 1, wherein the control device is configured or programmed to perform operations further comprising operations to:
perform the first scaling on the translational component and the rotational component using a first scaling value used in a previous control cycle;
calculate the rotation angle of the joint axis of the robot arm by performing the inverse kinematics calculation on the translational component and the rotational component after the first scaling is performed;
update the first scaling value such that the rotation speed of the joint axis of the robot arm becomes equal to or lower than the limit value; and calculate the rotation angle of the joint axis of the robot arm by performing the inverse kinematics calculation on the translational component and the rotational component using the homogenous transformation matrix after the first scaling is performed using the updated first scaling value.

3. The robotic surgical system according to claim 2, wherein
the robot arm includes the plurality of joint axes; and
the control device is configured or programmed to perform operations further comprising operations to:
calculate rotation angles of the plurality of joint axes;
calculate rotation speeds of the plurality of joint axes based on the rotation angles of the plurality of joint axes; and
change the first scaling value such that the first scaling value becomes smaller when the maximum rotation speed among the rotation speeds of the plurality of joint axes is equal to or higher than the limit value.

4. The robotic surgical system according to claim 3, wherein the control device is configured or programmed to perform operations further comprising operations to set, as a post-change first scaling value, a value obtained by dividing the first scaling value used in the previous control cycle by a value based on the maximum rotation speed.

5. The robotic surgical system according to claim 3, wherein the control device is configured or programmed to perform operations further comprising operations to set, as a post-change first scaling value, a value obtained by multiplying the smaller of a value obtained by dividing the first scaling value used in the previous control cycle by a value based on the maximum rotation speed and a predetermined value greater than a preset value of 1 by the first scaling value used in the previous control cycle.

6. The robotic surgical system according to claim 3, wherein the control device is configured or programmed to perform operations further comprising operations to calculate the translational component used in a current control cycle by linearly interpolating the translational component used in the previous control cycle and the translational component corresponding to the operation amount received by the operation unit based on a post-change first scaling value.

7. The robotic surgical system according to claim 3, wherein the control device is configured or programmed to perform operations further comprising operations to calculate the rotational component used in a current control cycle by performing spherical linear interpolation to interpolate the rotational component used in the previous control cycle and the rotational component corresponding to the operation amount received by the operation unit along a spherical surface based on a post-change first scaling value.

8. The robotic surgical system according to claim 2, wherein
the surgical instrument includes:
a shaft; and
a wrist joint that bends a jaw provided on a distal end side of the shaft; and
the control device is configured or programmed to perform operations further comprising operations to:
perform the first scaling on at least the rotational component of a plurality of joint axes of the surgical instrument including a roll rotation axis of the shaft and a rotation axis of the wrist joint;
calculate rotation angles of the plurality of joint axes of the surgical instrument by performing the inverse kinematics calculation on the translational component and the rotational component after the first scaling is performed;

update the first scaling value such that rotation speeds of the plurality of joint axes of the surgical instrument become equal to or lower than a limit value; and calculate the rotation angles of the plurality of joint axes of the surgical instrument by performing the inverse kinematics calculation on the translational component and the rotational component using the homogenous transformation matrix after the first scaling is performed using the updated first scaling value.

9. The robotic surgical system according to claim 2, wherein the control device is configured or programmed to perform operations further comprising operations to perform the first scaling on a virtual axis on which the surgical instrument rotates about a predetermined point.

10. The robotic surgical system according to claim 2, further comprising:

a receiver to receive a second scaling value for the translation of the surgical instrument by an operator; wherein the control device is configured or programmed to perform operations comprising operations to:

perform second scaling on the translational component based on the received second scaling value; and perform the first scaling on the translational component on which the second scaling has been performed.

11. The robotic surgical system according to claim 10, wherein the surgical instrument other than an endoscope is attached to the tip end of the robot arm;

the patient-side apparatus further includes a second robot arm having a tip end to which the endoscope is attached; and the control device is configured or programmed to perform operations comprising operations to set a third scaling value for the second robot arm in conjunction with the received second scaling value when the second scaling value for the robot arm is received by the receiver.

12. A control method of a robotic surgical system, the robotic surgical system comprising a patient-side apparatus including a robot arm having a tip end to which a surgical instrument is attached, an operator-side apparatus including an operation unit to receive an operation amount for the surgical instrument, and a control device configured or programmed to control translation and rotation of the surgical instrument based on the received operation amount, the control method comprising:

performing scaling on a translational component and a rotational component of the surgical instrument in the received operation amount; and calculating a rotation angle of a joint axis of the robot arm by performing an inverse kinematics calculation on the translational component and the rotational component after the scaling is performed, wherein the calculation of the rotation angle of the joint axis is performed by the inverse kinematics calculation using a homogenous transformation matrix including the translational component and the rotational component after the first scaling is performed, the scaling is performed with a scaling value such that a rotation speed of the joint axis of the robot arm becomes equal to or lower than a limit value, the controlling translation and rotation of the surgical instrument is performed based on the received operation amount and the scaling value, the calculating the rotation angle of the joint axis comprises calculating rotation angles of a plurality of joint axes of the robot arm; and calculating rotation speeds of the plurality of joint axes based on the rotation angles of the plurality of joint axes;

the scaling value is changed such that the scaling value becomes larger when a maximum rotation speed among rotation speeds of the plurality of joint axes is lower than the limit value, and the controlling translation and rotation of the surgical instrument is performed based on the received operation amount and the changed scaling value.

13. The control method of the robotic surgical system according to claim 12, wherein the performing the scaling includes performing the scaling such that a rotation speed of the joint axis of the robot arm becomes equal to or lower than a limit value.

14. The control method of the robotic surgical system according to claim 13, wherein the performing the scaling such that the rotation speed of the joint axis of the robot arm becomes equal to or lower than the limit value includes performing the scaling on at least the rotational component of the translational component and the rotational component using a scaling value used in a previous control cycle; and the control method further comprises updating the scaling value such that the rotation speed of the joint axis of the robot arm becomes equal to or lower than the limit value after calculating the rotation angle of the joint axis of the robot arm by performing the inverse kinematics calculation on the translational component and the rotational component after the scaling is performed; and the calculating the rotation angle of the joint axis of the robot arm includes calculating the rotation angle of the joint axis of the robot arm by performing the inverse kinematics calculation on the translational component and the rotational component using the homogenous transformation matrix after the scaling is performed using the updated scaling value.

15. The control method of the robotic surgical system according to claim 14, wherein the robot arm includes the plurality of joint axes;

the calculating the rotation angle of the joint axis of the robot arm includes calculating rotation angles of the plurality of joint axes and calculating rotation speeds of the plurality of joint axes based on the rotation angles of the plurality of joint axes; and the control method further comprises changing the scaling value such that the scaling value becomes smaller when the maximum rotation speed among the rotation speeds of the plurality of joint axes is equal to or higher than the limit value.

16. The control method of the robotic surgical system according to claim 15, wherein the changing the scaling value includes setting, as a post-change scaling value, a value obtained by dividing the scaling value used in the previous control cycle by a value based on the maximum rotation speed.

17. The control method of the robotic surgical system according to claim 15, further comprising:

changing the scaling value such that the scaling value becomes larger when the maximum rotation speed among the rotation speeds of the plurality of joint axes is lower than the limit value.

\* \* \* \* \*